United States Patent
Teasdale et al.

(10) Patent No.: US 9,192,677 B2
(45) Date of Patent: Nov. 24, 2015

(54) BIODEGRADABLE, WATER SOLUBLE AND PH RESPONSIVE POLY(ORGANO)PHOSPHAZENES

(75) Inventors: Ian P. Teasdale, Linz (AT); Ivo Nischanga, Linz (AT); Oliver Brüggemann, Wilhering (AT); Sandra Wilfert, Linz (AT)

(73) Assignee: JOHANNES KEPLER UNIVERSITÄT LINZ, Linz (AT)

( * ) Notice: Subject to any disclaimer, the term of this patent is extended or adjusted under 35 U.S.C. 154(b) by 145 days.

(21) Appl. No.: 13/821,228

(22) PCT Filed: Sep. 7, 2010

(86) PCT No.: PCT/EP2010/005482
§ 371 (c)(1),
(2), (4) Date: May 24, 2013

(87) PCT Pub. No.: WO2012/031609
PCT Pub. Date: Mar. 15, 2012

(65) Prior Publication Data
US 2013/0324490 A1  Dec. 5, 2013

(51) Int. Cl.
*A61K 47/34* (2006.01)
*A61K 31/337* (2006.01)
*A61K 33/24* (2006.01)
*A61K 31/704* (2006.01)
*A61K 47/48* (2006.01)
*A61K 31/4985* (2006.01)

(52) U.S. Cl.
CPC ............... *A61K 47/34* (2013.01); *A61K 31/337* (2013.01); *A61K 31/4985* (2013.01); *A61K 31/704* (2013.01); *A61K 33/24* (2013.01); *A61K 47/48107* (2013.01); *A61K 47/48215* (2013.01); *A61K 47/48223* (2013.01)

(58) Field of Classification Search
CPC . A61K 47/34; A61K 31/4985; A61K 31/704; A61K 33/24; A61K 31/337
USPC ...................................... 514/34, 81; 544/244
See application file for complete search history.

(56) References Cited

FOREIGN PATENT DOCUMENTS

| EP | 0425368 A2 | 2/1991 |
|---|---|---|
| WO | 2007/114549 A1 | 10/2007 |
| WO | 2008/130121 A1 | 10/2008 |

OTHER PUBLICATIONS

Ulbrich et al. Polymeric anticancer drugs with pH-controlled activation. Adv Drug Deliv Rev 56:1023-1050, 2004.*
Sohn, YS et al., "Poly- and Cyclophosphazenes as Drug Carriers for Anticancer Therapy," in Polyphosphazenes for Biomedical Applications, 249-275; Editor: Andrianov, AK; Wiley & Son, Hoboken, NJ; 2009.
Song, S-C et al., "A novel polymeric conjugate carrying two different anticancer drugs," Polym Int 48:627-629 (1999).
Kang, GD et al., "Controlled release of doxorubicin from thermosensitive poly(organophosphazene) hydrogels," International Journal of Pharmaceuticals 319 (2005) 29-36.
Chun, C et al., "Doxorubicin-polyphosphazene conjugate hydrogels for locally controlled delivery of cancer therapeutics," Biomaterials 30 (2009) 4752-4762.
Zheng C et al., "Novel polymersomes based on amphiphilic graft polyphosphazenes and their encapsulation of watersoluble anti-cancer drug," Polymer 50 (2009) 1173-1177.

* cited by examiner

Primary Examiner — Mark Shibuya
Assistant Examiner — Yih-Horng Shiao
(74) Attorney, Agent, or Firm — Sam K. Tahmassebi

(57) ABSTRACT

The present invention relates in general to the field of targeted drug delivery of anti-cancer drugs. More precisely, the present invention concerns polymer drug conjugates, namely, conjugates of poly(organo)phosphazenes and anti-cancer drugs, wherein the conjugates are suitable to selectively release anti-cancer drugs in tumor tissue. In addition, the present invention relates to a method for manufacturing such poly(organo)phosphazene molecule conjugates, to poly(organo)phosphazene molecule conjugates for use in medicine, in particular, to poly(organo)phosphazene molecule conjugates for use in the treatment of cancer, and to pharmaceutical compositions comprising such poly(organo)phosphazene molecule conjugates.

22 Claims, 9 Drawing Sheets

BIODEGRADABLE, WATER SOLUBLE AND PH RESPONSIVE POLY(ORGANO)PHOSPHAZENES

RELATED APPLICATIONS

This application is filed under 35 U.S.C. §371 as the U.S. national phase of International Application PCT/EP2010/005482, filed Sep. 7, 2010, which designated the U.S., the entire disclosure of which, including the drawings, is hereby incorporated herein by reference.

The present invention relates in general to the field of targeted drug delivery of anti-cancer drugs. More precisely, the present invention concerns polymer drug conjugates, namely, conjugates of poly(organo)phosphazenes and anti-cancer drugs, wherein the conjugates are suitable to selectively release anti-cancer drugs in tumor tissue. In addition, the present invention relates to a method for manufacturing such poly(organo)phosphazene molecule conjugates, to poly(organo)phosphazene molecule conjugates for use in medicine, in particular, to poly(organo)phosphazene molecule conjugates for use in the treatment of cancer, and to pharmaceutical compositions comprising such poly(organo)phosphazene molecule conjugates.

BACKGROUND OF THE INVENTION

Anti-cancer drugs used to control the growth of cancerous cells are commonly known to have severe side effects, since healthy tissue is always affected by these drugs.

For instance, anthracycline antibiotics, such as epirubicin, doxorubicin, daunorubicin, idarubicin and valrubicin, are a group of highly effective DNA intercalators derived from Streptomyces bacteria. Anthracycline antibiotics as some of the most effective anti-cancer drugs are used to treat a wide range of cancers, including leukemias, lymphomas, breast, uterine, ovarian, and lung cancers. However, anthracycline antibiotics also exhibit severe side effects due to their high toxicity towards healthy tissue. One of the main side effects of anthracycline antibiotics are cardiotoxicity, which considerably limits their usefulness, and vomiting.

Similar, taxanes and vinca alkaloids are anti-cancer drugs interfering with microtubule and mitotic spindle, respectively, and therefore, always affect both tumor and healthy tissue.

Beyond that, anti-cancer drugs are usually highly hydrophobic and, therefore, exhibit poor aqueous solubility. Thus, administration via blood stream is always critical. In addition, most anti-cancer drugs are rapidly eliminated from the body and therefore, have to be administered repeatedly in order to ensure constant therapeutic levels.

In order to avoid damage of healthy tissue in an effective way, it would be of great advantage to provide drug delivery systems suitable to selectively deliver and release anti-cancer drugs in tumor tissue. It would be of further advantage, if the desired drug delivery system were also suitable to enhance water solubility of hydrophobic anti-cancer drugs and to improve blood circulation time of anti-cancer drugs, and thus, suitable to be administered into the blood stream.

From the state of the art, it is known that water solubility of hydrophobic anti-cancer drugs generally can be improved and their toxicity reduced through conjugation to macromolecules. For instance, macromolecular drug carriers have been shown to improve the therapeutic index of anti-cancer drug molecules, improving their blood solubility and circulation time (Greco, F. et al, 2009, Haag, R. et al., 2006, Lee, C. C. et al., 2006, and Lammers, T. et al., 2010).

Furthermore, it is known that polymers with molecular weights above 30-50 kDa have decreased renal clearance and hence increased blood circulation time. In this respect, studies have also shown that an increased number of arms of the macromolecular carrier decrease renal filtration (Fox, M. E., et al., 2009).

Beyond that, macromolecules have been observed to accumulate in tumor tissue (Maeda, H. et al., 2000). This phenomenon is also known as the so-called enhanced permeability and retention (EPR) effect, which can regarded as passive tumor targeting.

The main reason for the EPR effect is thought to be higher vascular permeability of tumor tissue (tumor vasculature is, in principle, more permeable than healthy tissue), which allows large macromolecules to penetrate into the tumor. The haphazard structure of tumor tissue due to the fast growth of the cells and its poor lymphatic system means removal is slow, particularly for larger macromolecules, and therefore, leads to accumulation of these molecules. In addition, accumulation is observed to increase with increasing molecular weight (Maeda, H. et al., 2000).

However, at a particular threshold molecular weight (hydrodynamic volume)—depending on the used polymer and its macromolecular architecture—the macromolecules become too large to penetrate even porous tumor vasculature resulting in no further increase of the EPR effect.

In summary, choice and design of the macromolecule is of particular significance for its potential as drug delivery system of anti-cancer drugs.

Poly(organo)phosphazenes are a class of macromoleculare polymers of inorganic/organic hybrid type. Due to their synthetic flexibility, hydrolytic degradability and non-toxic degradation products, poly(organo)phosphazenes have been reported to have tremendous potential as materials for biomedical applications (El-Amin, S. F. et al., 2006). The polymer backbone of such poly(organo)phosphazenes consists of alternating phosphorus and nitrogen atoms (scheme 1), wherein organic substituents are linked to the phosphorus atoms as side chain groups.

Scheme 1: polymer backbone of poly(organo)phosphazenes consisting of alternating phosphorus and nitrogen atoms, R represents any suitable side chain.

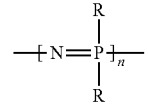

In this respect, U.S. Pat. No. 6,319,984 concerns biodegradable and thermosensitive poly(organo)phosphazenes having depsipeptide and amino acid ethylester side groups for use as drug delivery system in general. More specific poly(organo)phosphazenes are disclosed in US 2009/0181088 teaching poly(organo)phosphazene-bioactive molecule conjugates. These conjugates containing various bioactive molecules are biodegradable and thermosensitive poly(organo)phosphazenes with a functional group showing sol-gel phase transition upon temperature alteration. Due to this specific functional group the poly(organo)phosphazenes of US 2009/0181088 forms (after administration to the human body) a gel-phase at body temperature and, therefore, allows controlled release of the bioactive molecules. However, gelphase forming properties at body temperature means that these poly(organo)phosphazenes are not suitable to be administered into the blood stream.

US 2004/0219127 teaches polyphosphazene-platinum(II) conjugates having enhanced permeability and retention (EPR) effect to tumor tissues due to poly(ethylene glycol) and dispeptide ethyl esters introduced into the polyphosphazene backbone.

Beyond that Zheng et al., 2009, discloses self-assembly of polyphosphazenes into vesicle-like polymersomes and their encapsulation of water-soluble anti-cancer drug. However, these polyphosphazenes do not covalently link anti-cancer drugs.

All the above-mentioned conjugates of poly(organo)phosphazenes and anti-cancer drugs or polymersomes of polyphosphazenes encapsulating anti-cancer drugs accumulate in tumor tissues due to the EPR effect, in a more or less pronounced manner. Such accumulation in tumor tissue reduces side effects of the administered anti-cancer drugs, i.e. toxicity towards healthy tissue. However, in order to be effective against cancer, anti-cancer drugs also need to be selectively released from such conjugates and/or polymersomes while accumulating in tumor tissue.

Therefore, treatment of cancer would be much more effective and less toxic, if a drug delivery system could be provided suitable to selectively deliver and, additionally, to selectively release anti-cancer drugs in tumor tissue.

For this reason, it was an object of the present invention to provide novel poly(organo)phosphazene molecule conjugates suitable to selectively deliver and release anti-cancer drugs in tumor tissue. Furthermore, it was an object of the present invention to provide a process for preparing such poly(organo)phosphazene molecule conjugates and pharmaceutical compositions comprising such poly(organo)phosphazene molecule conjugates.

The object of the present invention, in one preferred embodiment thereof, is solved by a poly(organo)phosphazene molecule conjugate wherein the anti-cancer drug is covalently linked to the polymer backbone via a pH-sensitive linker.

Therefore, in a first aspect the present invention relates to a poly(organo)phosphazene molecule conjugate represented by formula 1:

formula 1

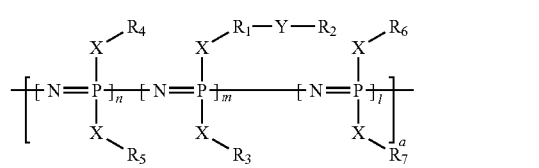

wherein, a represents a degree of polymerisation of the poly(organo) phosphazenes in the range of 1 and 150;

m is an integer between 1 and 150;

n and l are the same or different and each of n and l is independently from one another is an integer between 0 and 149;

X represents O, S or NH;

Y represents a pH sensitive functional group, wherein the pH sensitive functional group is selected from the group consisting of hydrazide, hydroxamate, imine, cyclic acetal and aconityl;

$R_1$ is selected from the group consisting of ($C_1$ to $C_{10}$)-alkyl, ($C_1$ to $C_{10}$)-alkenyl, ($C_1$ to $C_{10}$)-alkinyl, ($C_1$ to $C_{10}$)-alkoxy, ($C_1$ to $C_{10}$)-alkenoxy, ($C_1$ to $C_{10}$)-acyl, cycloalkyl, cycloalkenyl, aryl, arylalkyl, arylalkenyl, ($C_1$ to $C_{10}$)-heteroalkyl, ($C_1$ to $C_{10}$)-heteroalkenyl, ($C_1$ to $C_{10}$)-heteroalkinyl, ($C_1$ to $C_{10}$)-heteroalkoxy, ($C_1$ to $C_{10}$)-heteroalkenoxy, ($C_1$ to $C_{10}$)-heteroacyl, heterocycloalkyl, heterocycloalkenyl, heteroaryl, heteroarykalkenyl, heteroarylalkyls, and polyalkylene oxide;

$R_2$ represents an anti-cancer drug;

$R_3$, $R_4$, $R_5$, $R_6$ and $R_7$ are the same or different and each of $R_3$, $R_4$, $R_5$, $R_6$ and $R_7$ is independently from one another selected from the group consisting of $R_1$—Y—$R_2$, polyalkylene oxide, depsipeptide, amino acid alkyl ester, and a tumor targeting ligand.

Due to the functional group "Y" the poly(organo)phosphanes molecule conjugates of the present invention are suitable to selectively release anti-cancer drugs in tumor tissue. The extracellular pH of tumor tissue has a pH of about 4-6 and is, therefore, significantly lower than the extracellular pH of healthy tissue, which is approximately around 7.4. Since the poly(organo)phosphazene molecule conjugates of the present invention covalently link anti-cancer drugs via the pH sensitive functional group "Y", the anti-cancer drug of the conjugate will be only released in an acidic (tumor) environment. Thus, covalently linking of anti-cancer drugs via a pH sensitive functional group to poly(organo)phosphazenes allows the drug to be selectively released when the polymer-drug conjugate is transported and accumulated in tumor tissue.

Drugs can also be loaded onto macromolecular carriers via non-covalent interactions (for example hydrophobic or hydrogen-bonding interactions). However, a major problem of this method is that the drug molecules can leak out prematurely from the macromolecular carrier before it has reached the site of action. Some may leak out prior to the site of action and affect healthy tissue (Lee, MacKay et al. 2005)

Being able to covalently bind the drug to the polymer according to the present invention is therefore of significant advantage. However, the polymer must also be able to release its load rapidly when it reaches the site of action. If the drug molecule is directly bound to the polymer then biodegradation of the polymer is required before the drug is released (US Patent 20091811088). A polymer that degrades too quickly, however, will partially release its payload before reaching the site of action. In addition, employing a polymer that degrades more slowly, will lead to a slower release of the drug and delayed therapeutic action and a reduced efficacy, if polymer degradation is relied upon as the drug release mechanism.

Thus, the employment of an acid-sensitive linkage according to the present invention ensures—for the first time utilising poly(organo)phosphazenes—rapid release of the drug exclusively in the required environment, i.e. tumor tissue.

In this respect, a "pH-sensitive functional group" according to the present invention means any functional group which will respond to a pH lower than 6.5, i.e. which will be hydrolysed by a pH of lower than 6.5. Preferably, the pH-sensitive functional group of the present invention will respond to a pH lower than 6.5, 6.4, 6.3, 6.4, 6.3, 6.2, 6.1, 6.0, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1 and 4.0. More preferably, the pH-sensitive functional group of the present invention will respond to a pH in the range of 4.0 to 6.5, preferably, in the range of 4.5 to 6.0, more preferably, in the range of 4.5 to 6.0, and most preferably, in the range of 5.0 to 6.0. Thus, any functional group cleavable in an acidable environment (pH lower than 6.5, preferably lower than 6.0) known to the person skilled in the art would be suitable for the present invention. Preferably, the pH sensitive functional group is selected from the group consisting of hydrazide, hydroxamate, imine, cyclic acetal and aconityl.

In one preferred embodiment of the poly(organo)phosphazene molecule conjugate according to the present invention the pH sensitive group "Y" within formula 1 is represented by one formula 2 to 7 selected from the group consisting of formula 2
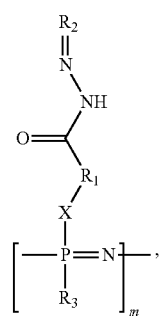

formula 3
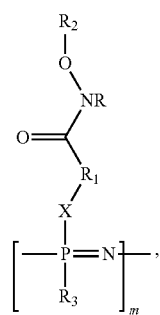

formula 4
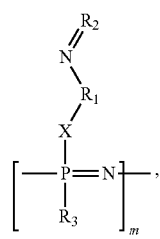

formula 5
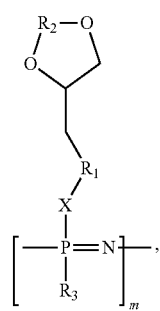

formula 6
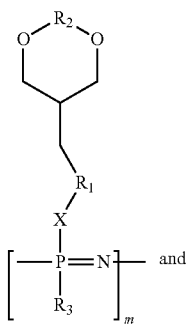
and formula 7
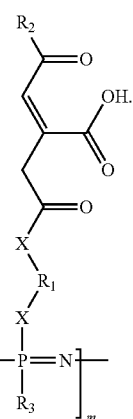

In order to receive such pH sensitive functional group "Y" a pH sensitive linker is reacted with the polymeric backbone selected from the group consisting of formula 8 to 13:

formula 8
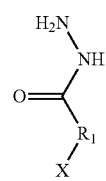

formula 9
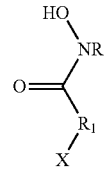

formula 10
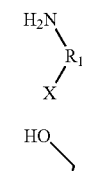

formula 11
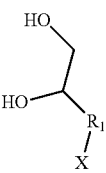

formula 12
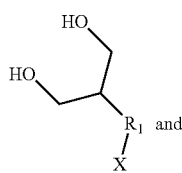
and formula 13
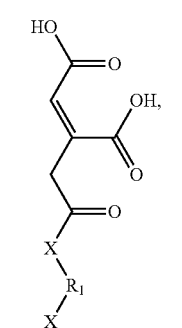

wherein X and $R_1$ are defined as above.

In another preferred embodiment of the poly(organo)phosphazene molecule conjugate according to the present invention $R_1$ is selected from the group consisting of ($C_1$ to $C_9$)-alkyl, ($C_1$ to $C_9$)-alkenyl, ($C_1$ to $C_9$)-alkinyl, ($C_1$ to $C_9$)-alkoxy, ($C_1$ to $C_9$)-alkenoxy, ($C_1$ to $C_9$)-acyl, cycloalkyl, cycloalkenyl, aryl, arylalkyl, arylalkenyl, ($C_1$ to $C_9$)-heteroalkyl, ($C_1$ to $C_{10}$)-heteroalkenyl, ($C_1$ to $C_9$)-heteroalkinyl, ($C_1$ to $C_9$)-heteroalkoxy, ($C_1$ to $C_9$)-heteroalkenoxy, ($C_1$ to $C_9$)-heteroacyl, heterocycloalkyl, heterocycloalkenyl, heteroaryl, heteroarykalkenyl, heteroarylalkyls, and polyalkylene oxide. Preferably, $R_1$ is selected from the group consisting of ($C_1$ to $C_8$)-alkyl, ($C_1$ to $C_8$)-alkenyl, ($C_1$ to $C_8$)-alkinyl, ($C_1$ to $C_8$)-alkoxy, ($C_1$ to $C_8$)-alkenoxy, ($C_1$ to $C_8$)-acyl, cycloalkyl, cycloalkenyl, aryl, arylalkyl, arylalkenyl, ($C_1$ to $C_8$)-heteroalkyl, ($C_1$ to $C_8$)-heteroalkenyl, ($C_1$ to $C_8$)-heteroalkinyl, ($C_1$ to $C_8$)-heteroalkoxy, ($C_1$ to $C_9$)-heteroalkenoxy, ($C_1$ to $C_8$)-heteroacyl, heterocycloalkyl, heterocycloalkenyl, heteroaryl, heteroarykalkenyl, heteroarylalkyls, and polyalkylene oxide. More preferably, $R_1$ is selected from the group consisting of ($C_1$ to $C_7$)-alkyl, ($C_1$ to $C_7$)-alkenyl, ($C_1$ to $C_7$)-alkinyl, ($C_1$ to $C_7$)-alkoxy, ($C_1$ to $C_7$)-alkenoxy, ($C_1$ to $C_7$)-acyl, cycloalkyl, cycloalkenyl, aryl, arylalkyl, arylalkenyl, ($C_1$ to $C_7$)-heteroalkyl, ($C_1$ to $C_7$)-heteroalkenyl, ($C_1$ to $C_7$)-heteroalkinyl, ($C_1$ to $C_7$)-heteroalkoxy, ($C_1$ to $C_7$)-heteroalkenoxy, ($C_1$ to $C_7$)-heteroacyl, heterocycloalkyl, heterocycloalkenyl, heteroaryl, heteroarykalkenyl, heteroarylalkyls, and polyalkylene oxide.

In the context of this invention, the term "alkyl" is understood as saturated, linear or branched hydrocarbons, which can occur unsubstituted, mono- or polysubstituted. In this respect, ($C_1$ to $C_7$)-alkyl represents C1-, C2-, C3-, C4-, C5-, C6- or C7-alkyl, ($C_1$ to $C_8$)-alkyl represents C1-, C2-, C3-, C4-, C5-, C6-, C7- or C8-alkyl, ($C_1$ to $C_9$)-alkyl represents C1-, C2-, C3-, C4-, C5-, C6-, C7, C8 or C9-alkyl, and ($C_1$ to $C_{10}$)-alkyl represents C1-, C2-, C3-, C4-, C5-, C6-, C7-, C8-, C9- or C10-alkyl. Alkyls of the present invention are, for example, methyl, ethyl, propyl, isopropyl, methylethyl, butyl, tert-butyl, 1-methylpropyl, 2-methylpropyl, 1,1-dimethylethyl, pentyl, 1,1-dimethylpropyl, 1,2-dimethylpropyl, 2,2-dimethylpropyl, 1-methylpentyl, if substituted also $CHF_2$, $CF_3$ or $CH_2OH$ etc.

In connection with the present invention—unless defined otherwise—the term "substituted" is understood as meaning replacement of at least one hydrogen radical by F, Cl, Br, I, $NH_2$, SH or OH. In this respect "monosubstituted" means the replacement of one hydrogen radical by F, Cl, Br, I, $NH_2$, SH or OH, wherein "polysubstituted" (more than once substituted) is means that the replacement takes effect both on different and on the same atoms several times, e.g. at least two times, with the same or different substituents, for example three times on the same C atom, as in the case of $CF_3$, or at different places, as in the case of e.g. —CH(OH)—CH=CH—$CHCl_2$. "Optionally at least monosubstituted" means either "monosubstituted", "polysubstituted" or—if the option is not fulfilled—"unsubstituted".

The term "alkenyl" as used herein is understood as unsaturated, linear or branched hydrocarbons containing at least one double bond, which can be unsubstituted, mono- or polysubstituted. In this respect, ($C_1$ to $C_7$)-alkenyl represents C1-, C2-, C3-, C4-, C5-, C6- or C7-alkenyl, ($C_1$ to $C_8$)-alkenyl represents C1-, C2-, C3-, C4-, C5-, C6-, C7- or C8-alkenyl, ($C_1$ to $C_9$)-alkenyl represents C1-, C2-, C3-, C4-, C5-, C6-, C7-, C8 or C9-alkenyl, and ($C_1$ to $C_{10}$)-alkenyl represents C1-, C2-, C3-, C4-, C5-, C6-, C7-, C8-, C9- or C10-alkenyl. "Alkenyls" of the present invention are, for example, methenyl, ethenyl, propenyl, isopropenyl, butenyl, isobutenyl, tert-butenyl, pentenyl, hexenyl, octenyl, butadienyl, and allenyl groups.

The term "alkinyl" as used herein is understood as unsaturated, linear or branched hydrocarbons containing at least one triple bond, which can be unsubstituted, mono- or polysubstituted. In this respect, ($C_1$ to $C_7$)-alkinyl represents C1-, C2-, C3-, C4-, C5-, C6- or C7-alkinyl, ($C_1$ to $C_8$)-alkinyl represents C1-, C2-, C3-, C4-, C5-, C6-, C7- or C8-alkinyl, ($C_1$ to $C_9$)-alkinyl represents C1-, C2-, C3-, C4-, C5-, C6-, C7, C8 or C9-alkinyl, and ($C_1$ to $C_{10}$)-alkinyl represents C1-, C2-, C3-, C4-, C5-, C6-, C7-, C8-, C9- or C10-alkenyl. "Alkinyls" of the present invention are, for example, methinyl, ethinyl, propinyl, isopropinyl, butinyl, isobutinyl, tert-butinyl, pentinyl, hexinyl, octinyl, and allinyl groups.

The terms "alkoxy" and "alkenoxy" as used herein refers to an alkyl and alkenyl, respectively, as defined above, which is linked to oxygen and which can be unsubstituted, mono- or polysubstituted. In this respect, ($C_1$ to $C_7$)-alkoxy represents C1-, C2-, C3-, C4-, C5-, C6- or C7-alkoxy, ($C_1$ to $C_8$)-alkoxy represents C1-, C2-, C3-, C4-, C5-, C6-, C7- or C8-alkoxy, ($C_1$ to $C_9$)-alkoxy represents C1-, C2-, C3-, C4-, C5-, C6-, C7-, C8 or C9-alkoxy, and ($C_1$ to $C_{10}$)-alkoxy represents C1-, C2-, C3-, C4-, C5-, C6-, C7-, C8-, C9- or C10-alkoxy. In addition, ($C_1$ to $C_7$)-alkenoxy represents C1-, C2-, C3-, C4-, C5-, C6- or C7-alkenoxy, ($C_1$ to $C_8$)-alkenoxy represents C1-, C2-, C3-, C4-, C5-, C6-, C7- or C8-alkenoxy, ($C_1$ to $C_9$)-alkenoxy represents C1-, C2-, C3-, C4-, C5-, C6-, C7-, C8 or C9-alkenoxy, and ($C_1$ to $C_{10}$)-alkenoxy represents C1-, C2-, C3-, C4-, C5-, C6-, C7-, C8-, C9- or C10-alkenoxy. Examples of "alkoxy" and "alkenoxy" of the present invention are methoxy, ethoxy, propoxy, butoxy, pentoxy, hexoxy, octoxy, groups, methenoxy, ethenoxy, propenoxy, butenoxy, pentenoxy, hexenoxy, octenoxy groups, etc.

The term "acyl" as used herein refers a functional group of R—(C=O)—, wherein R is an alkyl, alkenyl, alkinyl, cycloalkyl or cycloalkenyl as defined herein which can be unsubstituted, mono- or polysubstituted. Thus, the term "acyl" comprises linear, branched, cyclic, saturated or unstaturated hydrocarbons containing the functional group R—(C=O)—. In this respect, ($C_1$ to $C_7$)-acyl represents C1-, C2-, C3-, C4-, C5-, C6- or C7-acyl, ($C_1$ to $C_8$)-acyl represents C1-, C2-, C3-, C4-, C5-, C6-, C7- or C8-acyl, ($C_1$ to $C_9$)-acyl represents C1-, C2-, C3-, C4-, C5-, C6-, C7-, C8 or C9-acyl, and ($C_1$ to $C_{10}$)-acyl represents C1-, C2-, C3-, C4-, C5-, C6-, C7-, C8-, C9- or C10-acyl. Examples of "acyl" are methanoyl-, acetoyl-, ethanoyl-, propanoyl-, butanoyl-, malonyl-, benzoyl-groups, etc.

The term "cycloalkyl" or "cycloalkenyl" as used herein is a subdefinition of "alkyl" or "alkenyl" as defined above and is a carbon ring which can be unsubstituted, mono- or polysubstituted. The term "cycloalkyl" or "cycloalkenyl" typically refers to $C_3$, $C_4$, $C_5$, $C_6$, $C_7$, $C_8$, $C_9$ or $C_{10}$ cycloalkyl or cycloalkenyl, preferably refers to $C_4$, $C_5$, $C_6$, $C_7$, or $C_8$ cycloalkyl or cycloalkenyl and may include cyclopropyl, cyclobutyl, cyclopentyl, cyclohexyl, cyclooctyl, cyclopropenyl, cyclobutenyl, cyclopentenyl, cyclohexenyl, and cyclooctenyl groups.

A "heteroalkyl", "heteroalkenyl", "heteroalkinyl", "heteroyalkoxy", "heteroalkenoxy", "heteroacyl", "heterocycloalkyl", "heterocycloalkenyl", "heteroaryl", "heteroarylalkenyl", or a "heteroarylalkyls" are defined as an alkyl, an alkenyls an alkinyl, an alkoxy, an alkenoxy, an acyl, a cycloalkyl, a cycloalkenyl, an aryl, an arylalkenyl or an arylalkyl, as defined above, wherein said structures contain 0-7 heteroatoms selected from O, N or S, which replace at least one carbon atom in the alkyl, an alkenyls an alkinyl, an alkoxy, an alkenoxy, an acyl, a cycloalkyl or a cycloalkenyl as defined above.

The term "aryl" or "heteroaryl" as used herein refers to a 5- or 6-membered aromatic or heteroaromatic ring system containing 0-3 heteroatoms selected from O, N or S, a bicyclic 9- or 10-membered aromatic or heteroaromatic ring system ring containing 0-5 heteroatoms selected from O, N or S, or a tricyclic 13- or 14 membered aromatic or heteroaromatic ring system containing 0-7 heteroatoms selected from O, N or S and which can be unsubstituted, mono- or polysubstituted. The aromatic 6- to 14-membered ring systems include e.g. phenyl, naphthalene, indane, tetraline, and fluorene and the 5- to 10-membered aromatic heterocycloc ringsystems include e.g. imidazole, pyridine, indole, thiophene, benzopyranone, thiazole, furane, benzimidazole, chinolin, isochinoline, chinoxaline, pyrimidine, pyrazine, tetrazole, pyrazole, pyrrole, imidazole, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, and indoline.

Arylalkyl, arylalkenyls, heteroarylalkyl, heteroalkylalkenyl, heterocycloalkyl, heterocycloalkenyl moieties are each defined as their corresponding basic structures alkyl, alkenyl, aryl, heteroaryl, heteroalkyl, or heterocycloalkyl.

Any of the above alkyl, alkenyl, alkinyl, alkoxy, alkenoxy, acyl, cycloalkyl, cycloalkenyl, aryl, arylalkyl, arylalkenyls, heteroalkyl, heteroalkenyl, heteroalkinyl, heteroalkenyl, heteroalkoxy, heteroalkenoxy, heteroacyl, heterocycloalkyl, heterocycloalkenyl, heteroaryl, heteroarylalkyl groups may either be unsubstituted or (mono- or poly-) substituted with one or more non-interfering substituents, e.g., halogen, alkoxy, acyloxy, hydroxy, mercapto, carboxy, benzyloxy, phenyl, benzyl, or other functionality which may or has been suitably blocked with a protecting group so as to render the functionality non-interfering. Each substituent may be optionally substituted with additional non-interfering substituents. The term "non-interfering" characterizes the substituents as not adversely affecting any reactions to be performed in accordance with the process of this invention.

"Anti-cancer drugs" (also commonly known as "cytostatics") according to the present invention are any drug known in the art suitable to treat cancer, i.e. to treat malignancies, or cancerous growths in order to control the growth of cancerous cells.

In one preferred embodiment of the poly(organo)phosphazene molecule conjugate according to the present invention the anti-cancer drug of the present invention is selected from the group consisting of antibiotics, si-RNA, antisense RNA, alkylating agents, platinum analogues, intercalating drugs, antibiotics, mitotic inhibitors, taxanes, topoisomerase inhibitors, anti-metabolites, hydroxycarbamid, podophyllotoxin, enzymes, hormones, tumor necrosis factor, biological response modifiers and any other known cytostatic.

Preferably, the anti-cancer drug of the poly(organo)phosphazene molecule conjugate according to the present invention is selected from the group consisting of aminolevulinic acic, abarelix, abiraterone, aclacinomycins, agatolimoc, alitretinoin, altretamine, americium, amifostine, aminoglutethimice, aminopterin, amrubicin, amsacrine, anastrozole, ancitabine, aplicine, aprinocarsen, arsenic trioxice, arzoxifene, asparaginase, atrasentan, axitinib, azaciticine, batimastat, belinostat, belotecan, bencamustine, bevacizumab, bexarotene, bicalutamice, biricocar, bisantrene, bleomycins, bortezomibm bosutinib, brostallicin, broxuricine, buserelin, busulfan, cabazitaxel, cactinomycin, calcitriol, californium, canertinib, canfosfamice, capecitabine, carboplatin, carboquone, carmofur, carmustine, carubicin, cetrorelix, cetuximab, chlorambucil, chlormacinone acetate, chlornaphazine, chlorozotocin, chromic phosphate, cilengitice, cintrecekin besucotox, cisplatin, clacribine, clofarabine, cobalt, contusugene lacenovec, cositecan, cyclophosphamice, cytarabine, cacarbazine, cactinomycin, casalini, caunorubicin, cecitabine, cegarelix, cehycroequol, cenileukin ciftitox, cenopterin, ciaziquone, ciethylstilbestrol, cimesna, cocetaxel, coxifluricine, coxorubicin, croloxifene, cromostanolone, ecteinascicins, ecatrexate, ecotecarin, ecotreotice, ecrecolomab, efaproxiral, eflornithine, elliptinium acetate, eniluracil, enocitabine, enzastaurin, epirubicin, epitiostanol, epratuzumab, eribulin, erlotinib, estramustine, etanicazole, ethiocizec oil, etoglucic, etoposice, everolimus, exatecan, exemestane, facrozole, fenretinice, flavopiricol, floxuricine, flucarabine, fluorouracil, flutamice, folinic acic, formestane, fosfestrol, fotemustine, fulvestrant, gallium nitrate, gefitinib, gemcitabine, gemtuzumab ozogamicin, glufosfamice, golc, racioactive, colloical, goserelin, hexestrol, histamine, histrelin, homoharringtonine, hycroxyurea, ibritumomab tiuxetan, icarubicin, icoxifene, ifosfamice, imatinib, imiquimoc, improsulfan, incisulam, interferon-, interleukin-2, iobenguane, irinotecan, irofulven, ixabepilone, kahalalice f, lanreotice, lapatinib, laromustine, lentinan, letrozole, leuprolice, liarozole, lobaplatin, lomustine, lonafarnib, lonicamine, marimastat, mechlorethamine oxice hycrochlorice, mechlorethamine, mecroxyprogesterone, megestrol acetate, melphalan, mepact, mepitiostane, mesna, methotrexate, methyl aminolevulinate, micostaurin, miltefosine, mitobronitol, mitoguazone, mitolactol, mitomycins, mitotane, mitoxantrone, mofarotene, motesanib, motexafin gacolinium, motexafin lutetium, nelarabine, Neovastat® (aeterna), nilutamice, nimustine, ninopterin, nitra crine, nolatrexec, norcihycroguaiaretic acic, oblimersen socium, ofatumumab, olaparib, olivomycins, onapristone, oregovomab, oxaliplatin, paclitaxel poliglumex, paclitaxel, palifermin, panitumumab, panobinostat, pazopanib, pemetrexec, pentostatin, peplomycin, perfosfamice, perifosine, pertuzumab, picoplatin, pipobroman, piposulfan, pirarubicin, piritrexim, pixantrone, plicamycin, polyestraciol phosphate, porfimer socium, porfiromycin, potassium arsenite, precnimustine, prinomastat, procarbazine, propagermanium, Psk® (kureha chemical incustry co., ltc. pharmaceutical civ.; kureha), pteropterin, racium, racon, raltitrexec, ranimustine, ranpirnase, razoxane, retinoic acic, rituximab, romicepsin, roquinimex, rubitecan, samarium 153sm lexicronam, satraplatin, seliciclib, seocalcitol, sipuleucel-t, sizofiran, sobuzoxane, socium iocice, racioactive, socium phosphate, radioactive, sorafenib, spirogermanium, streptozocin, strontium chlorice, strontium, sunitinib, talaporfin, tamibarotene, tamoxifen, tariquicar, tegafur, temoporfin, temozolomice, temsirolimus, teniposice, tesmilifene, testolactone, thiamiprine, thioguanine, tiazofurin, tipifarnib, tirapazamine, topotecan, toremifene, tositumomab, trabecersen, trastuzumab, trichlormethine, triethylenemelamine, triethylenephosphoramice, triethylenethiophosphoramice, trilostane, trimetrexate, triptorelin, trofosfamice, troxacitabine, ubenimex, uracil mustarc, urecepa, valrubicin, valspocar, vancetanib, catalani, vinblastine, vincristine, vincesine, vinflunine, vinorelbine, vorinostat, vorozole, zinostatin, zorubicin, zosuquicar, 6-azauricine, 6-mercaptopurine and 9-aminocamptothecin.

More preferably, the anti-cancer drug of the poly(organo) phosphazene molecule conjugate according to the present invention is selected from the group consisting of epirubicin, doxorubicin, daunorubicin, idarubicin and valrubicin.

In one particular preferred embodiment of the poly(organo)phosphazenes of the present invention the anti-cancer drug is epirubicin. In this respect the release of epirubicin from the polymer-drug conjugates was simulated under physiological conditions at 37° C. in a pH 7.4 phosphate buffer and in an acidic medium at pH 5 in an acetate buffer solution. At pH 5 a steady release of the drug molecule from the polymer was observed, with 100% release from the polymer-drug conjugate being observed within 15 hours. Meanwhile, only minimal release was observed within a period of 24 h from the polymers at pH 7.4 (FIG. 2).

The term "polyalkylene oxide" according to the present invention is a polymer composed of repeating oxyalkylene units (—OR—), for example $CH_2O$, $C_2H_6O$, $C_3H_6O$, $C_4H_8O$, or combinations thereof, from 2 to 800 repeat units, preferably 10-50 repeat units. They can be linear or branched, but must be overall hydrophilic. Preferred polymers comprise majority (>50%) —$C_2H_6O$— units. The polymers should be end-capped with a non-nucleophilic group at one end, preferably $CH_3O$ or $C_2H_7O$ and a nucleophilic moeity at the other end, preferably $NH_2$.

Poly(organo)phosphazenes comprising polyalkylene oxides exhibit enhanced water solubility, hydrodynamic volume and number of arms to the polymers. As already mentioned above an increased number of arms of the macromolecular carrier decrease renal filtration and therefore, exhibit increased blood circulation time (Fox, M. E., et al., 2009).

Therefore, in one preferred embodiment of the poly(organo)phosphazenes of the present invention, $R_3$ and/or $R_4$ and/or $R_5$ and/or $R_6$ and/or $R_7$ represents a polyalkylene oxide as defined above.

In one preferred embodiment of the poly(organo)phosphazene molecule conjugate according to the present invention the polyalkylene oxide is selected from the group consisting of polyether, methoxypolyether, ethoxypolyether, polyethylene oxide, polypropylene oxide, polybutylene oxide, polyethylene glycol, polypropylene glycol, polybutylene glycol, methoxypolyethylene oxide, methoxypolypropylene oxide, methoxypolybutylene oxide, methoxypolyethylene glycol, methoxypolypropylene glycol, methoxypolybutylene glycol, ethoxypolyethylene oxide, ethoxypolypropylene oxide, ethoxypolybutylene oxide, ethoxypolyethylene glycol, ethoxypolypropylene glycol, ethoxypolybutylene glycol, poly(ethylene oxide-co-propylene oxide), poly(ethylene glycol-co-propylene glycol), poly(ethylene oxide-co-butylene oxide), poly(ethylene glycol-co-butylene glycol), poly(propylene oxide-co-butylene oxide), poly(propylene glycol-co-butylene glycol), methoxypoly(ethylene oxide-co-propylene oxide), methoxypoly(ethylene glycol-co-propylene glycol), methoxypoly(ethylene oxide-co-butylene oxide), methoxypoly(ethylene glycol-co-butylene glycol), methoxypoly(propylene oxide-co-butylene oxide), methoxypoly(propylene glycol-co-butylene glycol), ethoxypoly(ethylene oxide-co-propylene oxide), ethoxypoly(ethylene glycol-co-propylene glycol), ethoxypoly(ethylene oxide-co-butylene oxide), ethoxypoly(ethylene glycol-co-butylene glycol), ethoxypoly(propylene oxide-co-butylene oxide) and ethoxypoly(propylene glycol-co-butylene glycol).

"Depsipetide" according to the present invention means a peptide, wherein one or more peptide linkages are substituted by ester linkages, i.e. a peptide in which one or more of the amide (—CONHR—) bonds are replaced by ester (COOR) bonds. In one preferred embodiment of the poly(organo) phosphazene molecule conjugate according to the present invention depsipeptide is selected from the group consisting of beativericin, morpholinedione, valinomycin, Depsipeptide A, Depsipeptide B, ethyl-2-(O-glycyl)glycolate and ethyl-2-(O-glycyl)lactate.

The term "amino acid alkyl ester" according to the present invention is an alkyl derivative of an amino acid, i.e. an ester formed by an amino acid and an alkanol, wherein the alkanol is an alkyl, as defined above, carrying an OH-moiety, preferably an ($C_1$ to $C_{10}$)-alkyl. In this respect, an amino acid is any natural or non-natural amino acid selected from the group consisting of Alanine, Arginine, Asparagine, Aspartic Acid, Cysteine, Glutamic Acid, Glutamine, Glycine, Histidine, Isoleucine, Leucine, Lysine, Methionine, Phenylalanine, Proline, Serine, Threonine, Tryptophan, Tyrosine, Valine, 2-Aminoadipic acid, 3-Aminoadipic acid, beta-Alanine, beta-Aminopropionic acid, 2-Aminobutyric acid, 4-Aminobutyric acid, piperidinic acid, 6-Aminocaproic acid, 2-Aminoheptanoic acid, 2-Aminoisobutyric acid, 3-Aminoisobutyric acid, 2-Aminopimelic acid, 2,4 Diaminobutyric acid, Desmosine, 2,2'-Diaminopimelic acid, 2,3-Diaminopropionic acid, N-Ethylglycine, N-Ethylasparagine, Hydroxylysine, allo-Hydroxylysine, 3-Hydroxyproline, 4-Hydroxyproline, Isodesmosine, allo-Isoleucine, N-Methylglycine, sarcosine, N-Methylisoleucine, 6-N-Methyllysine, N-Methylvaline, Norvaline, Norleucine, Ornithine Selenocysteine, and Taurine.

It is known that polymers with a molecular weight above the renal clearance limit will accumulate in the body, and, therefore, lead to damaging side effects. Thus, it is extremely desirable that polymers used for drug delivery applications degrade under physiological conditions. However, a major disadvantage of many organic polymers is their lack of biodegradability. In this respect, it is well-reported that poly(organo)phosphanes degrade to biocompatible products under physiological conditions. The rate of degradation can vary greatly, depending on the properties of the side-substituents and hydrophilicity of the polymer. (Allock, H. R. et al., 1977; Ibim, S.E.M. et al., 1997). This can be readily utilized to give a broad spectrum of polymers with very different rates of degradation. In addition to the corresponding side groups, polyphosphazenes have been shown to degrade to low toxicity compounds including ammonia and phosphates (Allock, H. R. et al., 1994). In particular, hydrophilic amino substituted polyphosphazenes are known to be hydrolytically unstable and the stability can be tailored by careful choice of substituents such as depsipeptides or amino acid esters.

Therefore, in one preferred embodiment of the poly(organo)phosphazenes of the present invention, $R_3$ and/or $R_4$ and/or $R_5$ and/or $R_6$ and/or $R_7$ represents a depsipeptide as defined above.

In another preferred embodiment of the poly(organo)phosphazenes of the present invention, $R_3$ and/or $R_4$ and/or $R_5$ and/or $R_6$ and/or $R_7$ represents an amino acid alkyl ester as defined above.

It has been reported that the rate of degradation of polyphosphazenes can be altered significantly by careful choice of substituents. In particular, the incorporation of amino acid side chains has been shown to considerably decrease the hydrolytic stability of hydrophilic poly(organo)phosphazenes (Vandorpe, J. et al., 1996, Andrianov, A. K. et al., 2006). In this respect, a series of polymers were synthesised via sequential addition of linker, PEO-PPO-$NH_2$ and then ethyl glycinate ester side chains in varying ratios. As shown in FIG. 3, the degradation is considerably accelerated upon incorporation of ethyl glycinate side groups. After 2 weeks, the $M_n$ of polymer 7, in which around 47% of the chlorine atoms were substituted with ethyl glycinate groups, was reduced to 66% of its original value, whereby polymer 2 had a $M_n$ value 80% of its original.

A "tumor targeting ligand" according to the present invention means any substance specifically targeting tumor-specific antigens and/or tumor-specific receptors. For instance, the folate receptor has been shown to be over-expressed in many human cancers (Lu, Y. and Low, P. S., 2002). Thus, folic acid binding to the folate receptor is a "tumor targeting ligand".

Therefore, in one preferred embodiment of the poly(organo)phosphazenes of the present invention, $R_3$ and/or $R_4$ and/or $R_5$ and/or $R_6$ and/or $R_7$ represents an amino acid alkyl ester as defined above.

Poly(organo)phosphazene molecule conjugates of the present invention comprising at least one tumor targeting ligand have the advantage to selectively target tumor tissue. In one preferred embodiment of the poly(organo)phosphazene molecule conjugate according to the present invention the tumor targeting ligand is selected from the group consisting of biotin, folic acid, vitamin B12, riboflavin, hyaluronic acid, monoclonal antibodies targeting tumor-specific antigens and/or tumor-specific receptors and variants thereof, polyunsaturated fatty acids, aptamers targeting tumor-specific antigens and/or tumor-specific receptors, oligopeptides targeting tumor-specific antigens and/or tumor-specific receptors. In this respect "tumor-specific antigen or receptor" means any antigen and/or receptor which specifically is expressed within tumor tissue.

In one preferred embodiment of the poly(organo)phosphazene molecule conjugate according to the present invention the sum of a, m, n and l is ≤150, preferably the sum of a, m, n and l is ≤140, ≤130, ≤120, ≤110, ≤100, ≤90, ≤80. More preferably, the sum of a, m, n and l is in the range of 1 to 150, 1 to 140, 1 to 130, 1 to 120, 1 to 110, 1 to 100, 1 to 90, 1 to 80, and 1 to 75, alternatively, the sum of a, m, n and l is in the range of 5 to 150, 5 to 140, 5 to 130, 5 to 120, 5 to 110, 5 to 100, 5 to 90, 5 to 80, and 5 to 75, alternatively, the sum of a, m, n and l is in the range of 10 to 150, 10 to 140, 10 to 130, 10 to 120, 10 to 110, 10 to 100, 10 to 90, 10 to 80, and 10 to 75, alternatively, the sum of a, m, n and l is in the range of 15 to 150, 15 to 140, 15 to 130, 15 to 120, 15 to 110, 15 to 100, 15 to 90, 15 to 80, and 15 to 75, alternatively, the sum of a, m, n and l is in the range of 20 to 150, 20 to 140, 20 to 130, 20 to 120, 20 to 110, 20 to 100, 20 to 90, 20 to 80, and 20 to 75, alternatively, the sum of a, m, n and l is in the range of 25 to 150, 25 to 140, 25 to 130, 25 to 120, to 110, 25 to 100, 25 to 90, 25 to 80, and most preferably, the sum of a, m, n and l is in the range of 25 to 75.

In one preferred embodiment of the poly(organo)phosphazene molecule conjugate according to the present invention "a" represents a degree of polymerisation of the poly(organo)phosphazenes in the range of 1 to 150, 1 to 140, 1 to 130, 1 to 120, 1 to 110, 1 to 100, 1 to 90, 1 to 80, and 1 to 75, alternatively, "a" represents a degree of polymerisation of the poly(organo)phosphazenes in the range of 5 to 150, 5 to 140, 5 to 130, 5 to 120, 5 to 110, 5 to 100, 5 to 90, 5 to 80, and 5 to 75, alternatively, "a" represents a degree of polymerisation of the poly(organo)phosphazenes in the range of 10 to 150, 10 to 140, 10 to 130, 10 to 120, 10 to 110, 10 to 100, 10 to 90, 10 to 80, and 10 to 75, alternatively, "a" represents a degree of polymerisation of the poly(organo)phosphazenes in the range of 15 to 150, 15 to 140, 15 to 130, 15 to 120, 15 to 110, 15 to 100, 15 to 90, 15 to 80, and 15 to 75, alternatively, "a" represents a degree of polymerisation of the poly(organo)phosphazenes in the range of 20 to 150, 20 to 140, 20 to 130, 20 to 120, 20 to 110, 20 to 100, 20 to 90, 20 to 80, and 20 to 75, alternatively, "a" represents a degree of polymerisation of the poly(organo)phosphazenes in the range of 25 to 150, 25 to 140, 25 to 130, 25 to 120, 25 to 110, 25 to 100, 25 to 90, 25 to 80, and most preferably, "a" represents a degree of polymerisation of the poly(organo)phosphazenes in the range of 25 to 75.

In another preferred embodiment of the poly(organo)phosphazene molecule conjugate according to the present invention "m" represents an integer between 1 to 150, 1 to 140, 1 to 130, 1 to 120, 1 to 110, 1 to 100, 1 to 90, 1 to 80, and 1 to 75, alternatively, "m" represents an integer between 5 to 150, 5 to 140, 5 to 130, 5 to 120, 5 to 110, 5 to 100, 5 to 90, 5 to 80, and 5 to 75, alternatively, "m" represents an integer between 10 to 150, 10 to 140, 10 to 130, 10 to 120, 10 to 110, 10 to 100, 10 to 90, 10 to 80, and 10 to 75, alternatively, "m" represents an integer between 15 to 150, 15 to 140, 15 to 130, 15 to 120, 15 to 110, 15 to 100, 15 to 90, 15 to 80, and 15 to 75, alternatively, "m" represents an integer between 20 to 150, 20 to 140, 20 to 130, 20 to 120, 20 to 110, 20 to 100, 20 to 90, 20 to 80, and 20 to 75, alternatively, "m" represents an integer between 25 to 150, 25 to 140, 25 to 130, 25 to 120, 25 to 110, 25 to 100, 25 to 90, 25 to 80, and most preferably, "m" represents an integer between 25 to 75.

In one preferred embodiment of the poly(organo)phosphazene molecule conjugate according to the present invention "n" and "l" are the same or different and each of n and l is independently from one another an integer between 1 and 149, preferably, between 1 to 139, 1 to 129, 1 to 119, 1 to 109, 1 to 99, 1 to 89, 1 to 79, and 1 to 74, alternatively, "n" and "l" are the same or different and each of n and l is independently from one another an integer between 1 to 145, 1 to 140, 1 to 135, 1 to 130, 1 to 125, 1 to 120, 1 to 115, 1 to 110, 1 to 105, 1 to 100, 1 to 95, 1 to 90, 1 to 85, 1 to 75, and 1 to 70, alternatively, "n" and "l" are the same or different and each of n and l is independently from one another an integer between 5 to 145, 5 to 140, 5 to 135, 5 to 130, 5 to 125, 5 to 120, 5 to 115, 5 to 110, 5 to 105, 5 to 100, 5 to 95, 5 to 90, 5 to 85, 5 to 75, and 5 to 70, alternatively, "n" and "l" are the same or different and each of n and l is independently from one another an integer between 10 to 145, 10 to 140, 10 to 135, 10 to 130, 10 to 125, 10 to 120, 10 to 115, 10 to 110, 10 to 105, 10 to 100, 10 to 95, 10 to 90, 10 to 85, 10 to 75, and 10 to 70, alternatively, "n" and "l" are the same or different and each of n and l is independently from one another an integer between 15 to 145, 15 to 140, 15 to 135, 15 to 130, 15 to 125, 15 to 120, 15 to 115, 15 to 110, 15 to 105, 15 to 100, 15 to 95, 15 to 90, 15 to 85, 15 to 75, and 15 to 70, alternatively, "n" and "l" are the same or different and each of n and l is independently from one another an integer between 20 to 145, 20 to 140, 20 to 135, 20 to 130, to 125, 20 to 120, 20 to 115, 20 to 110, 20 to 105, 20 to 100, 20 to 95, 5 to 90, 20 to 85, 20 to 75, and 20 to 70, alternatively, "n" and "l" are the same or different and each of n and l is independently from one another an integer between 25 to 145, 25 to 140, 25 to 135, 25 to 130, 25 to 125, 25 to 120, 25 to 115, 25 to 110, 25 to 105, 25 to 100, 25 to 95, to 90, 25 to 85, 25 to 75, and 25 to 70.

In another preferred embodiment of the poly(organo)phosphazene molecule conjugate according to the present invention X is NH.

In another preferred embodiment of the poly(organo)phosphazenes of the present invention, $R_3$ and/or $R_4$ and/or $R_5$ and/or $R_6$ and/or $R_7$ represents $R_1$—Y—$R_2$, wherein $R_1$—Y—$R_2$ is defined as above.

As already outlined above, the molecular architecture and hydrodynamic volume of the polymer plays a crucial role in the pharmacokinetics and in-vivo distribution of polymeric drug carriers (Fox, M. E., et al., 2009), accurate control of both molecular weight and dispersity is an important factor for polymer therapeutics.

In this respect, the polydispersity index (PDI) is the weight average molecular weight divided by the number average molecular weight and, therefore, a measure of the distribution of molecular mass in a given polymer sample. Thus, the PDI indicates the distribution of individual molecular masses in a batch of polymers. A PDI equal to or little above 1 indicates that the distinct polymer chains in a given polymer sample approach uniform chain length, i.e. only one length of polymer is present. In contrast, a PDI around 10 to 20 refers to a batch of polymers having polymer chains varying in chain lengths over a wide range of molecular masses.

Therefore, in one preferred embodiment of the poly(organo)phosphazenes of the present invention the poly(organo) phosphazene has a polydispersity of 1.8 or less, preferably, the poly(organo)phosphazene has a polydispersity of 1.7 or less, more preferably of 1.6 or less, even more preferably of 1.5 or less and most preferably of 1.4 or less.

In this respect, it should be noted that the major precursor of poly(organo)phosphazenes is dichloropolyphosphazene. Dichloropolyphosphazene is extremely hydrolytically unstable, however, can be readily substituted to give a wide range of stable poly(organo)phosphazenes with an extremely wide range of properties.

So far, the most developed method of synthesis for preparation of dichloropolyphosphazene is the so-called thermal ring-opening polymerisation of hexachlorophosphazene at 250° C. This method does not allow any controlling of the molecular weight of the synthesized polymers. Therefore, dichloropolyphosphazenes synthesized by thermal ring-opening polymerisation generally have high molecular weights ($M_w$>10$^6$ daltons) and, in addition, broad polydispersities, i.e. polydispersity indexes (PDI) up to 19. Limited control of the molecular weight utilizing thermal ring-opening polymerisation can be achieved by the use of catalysts such as $OP(OPh)_3/BCl_3$ or $AlCl_3$. However, high temperatures are still required which also result in broad polydispersity, as it is the case, for example, for the condensation polymerisation of $Cl_3P=(O)Cl_2$. By high temperature reaction of $PCl_5$ with $NH_4Cl$ (Allcock, H. R., et al., 1996) only low molecular weight dichloropolyphosphazene with limited molecular weight control can be achieved.

To date synthesis of the precursor polymer dichloropolyphosphazene with controlled molecular weights and narrow molecular weight distribution, i.e. narrow polydispersities, such as, for example PDIs in the range of 1.1-1.8, preferably, 1.1-1.6, more preferably, 1.1-1.4 according to the present invention, is enabled by the room temperature living cationic polymerisation of chlorophosphoranimine, pioneered by Allcock and Manners, (Allcock, H. R., et al., 1996 and Blackstone, V. et al., 2009) and unavailable by any other methods as disclosed in U.S. Pat. No. 5,698,664 or U.S. Pat. No. 5,914,388.

Thus, the development of a living polymerisation route to polyphosphazenes was a key advancement allowing access to block copolymers (Nelson, J. M., et al., 1998 and Matyjaszewski, K. et al., 1993) star-branched and dendritic polymers based on polyphosphazenes (Nelson, J. M., et al., 1997 and Cho, S. Y., et al. 2007).

Therefore, in a second aspect the present invention concerns a process for preparing a poly(organo)phosphazenes conjugates according to the present invention, comprising cationic living polymerisation of chlorophosphoramines.

In one preferred embodiment, the present invention relates to a process for preparing a poly(organo)phosphazene molecule conjugate according to the present invention, comprising the steps of:
 a) preparation of dichloropolyphosphazenes by living cationic polymerisation of chlorophosphoranimes;
 b) substitution of at least one chlorine atom of the dichloropolyphosphazenes of step a) with a pH sensitive linker; and
 c) covalently binding an anti-cancer drug to the pH sensitive linker.

"Living cationic polymerisation" is known in the art. In one preferred embodiment of the process for preparing a poly (organo)phosphazene conjugate according to the present invention, dichloropolyphosphazenes are synthesised by the polymerisation of chlorophosphoranime utilising living polymerisation according to Allock, H. R., 1996 and U.S. Pat. No. 5,698,664. This simple room temperature polymerisation results in polymers with narrow polydispersities, i.e. polydispersities of 1.8 or less.

In one preferred embodiment of the process according to the present invention, the polymerised dichloropolyphosphazene of step a) of the process of the present invention has a polydispersity of 1.8 or less, preferably, of 1.7 or less, more preferably, of 1.6 or less, even more preferably of 1.5 or less and most preferably of 1.4 or less. In one preferred embodiment the polymerised dichloropolyphosphazene of step a) of the process of the present invention has a polydispersity in the range of 1.0 to 1.8, preferably, 1.1 to 1.7, more preferably, in the range of 1.2 to 1.6 and most preferably, in the range of 1.3 to 1.5.

The polymers in this state are very hydrolytically unstable, due to the labile chlorine groups and must be stored in a dry, inert atmosphere. It is also critical that all reagents used in the polymerisation and subsequent reactions are extremely dry as $H_2O$ reacts readily with dichloropolyphosphazenes.

However, the advantage of these labile chlorine atoms is that they can then be readily substituted with the desired nucleophilic substituents, such as alcohols, thiols or amines. In one preferred embodiment of the present invention, amine-capped organic reagents in THF (wherein any dry polar solvent, such as dioxane would be also suitable) and with an equimolar amount of triethylamine as a scavenger for the HCl by-product are used.

Scheme 2: Living polymerisation of poly(organo)phosphazenes.

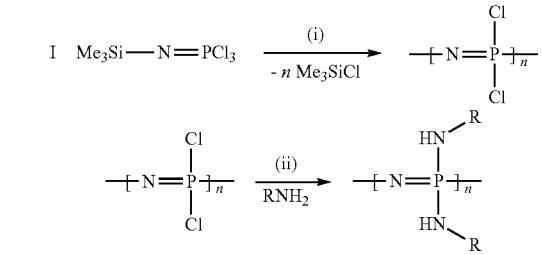

Reagents and conditions: (i) PCl$_5$, CH$_2$Cl$_2$, RT; (ii) NEt$_3$, THF, RT

In one preferred embodiment of the process of the present invention the pH sensitive linker can be any linker resulting in a "pH sensitive functional group" as defined above, i.e a "pH-sensitive functional group" which will respond to a pH lower than 6.5, i.e. which will be hydrolysed by a pH of lower than 6.5. Preferably, the pH-sensitive functional group of the present invention will respond to a pH lower than 6.5, 6.4, 6.3, 6.4, 6.3, 6.2, 6.1, 6.0, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1 and 4.0. More preferably, the pH-sensitive functional group of the present invention will respond to a pH in the range of 4.0 to 6.5, preferably, in the range of 4.5 to 6.0, more preferably, in the range of 4.5 to 6.0, and most preferably, in the range of 5 to 6.0. Thus, any functional group cleavable in an acidable environment (pH lower than 6.5, preferably lower than 6.0) known to the person skilled in the art would be suitable for the present invention. Preferably, the pH sensitive functional group is selected from the group consisting of hydrazide, hydroxamate, imine, cyclic acetal and aconityl.

In one particular preferred embodiment for preparing a poly(organo)phosphazene molecule conjugate according to the present invention the pH sensitive linker is selected from the group consisting of formula 8 to 13

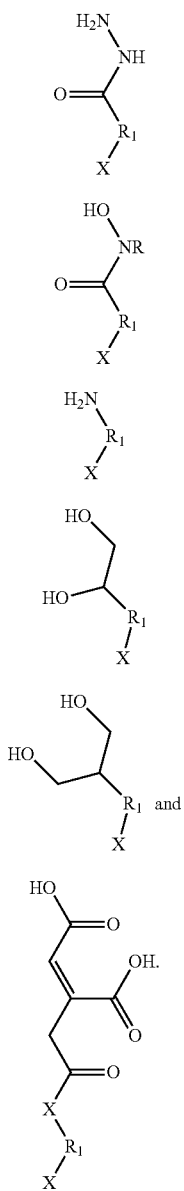

formula 8 formula 9 formula 10 formula 11 formula 12 and formula 13 wherein X and R1 are defined as above.

In one particular preferred embodiment for preparing a poly(organo)phosphazene molecule conjugate according to the present invention the pH sensitive linker is selected from the group consisting of formula 14 to 19

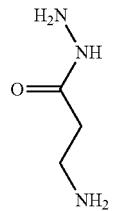

formula 14

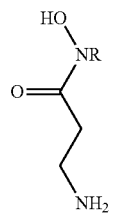

formula 15

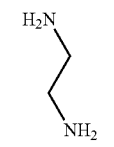

formula 16

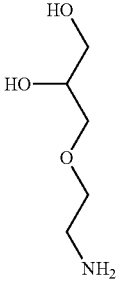

formula 17

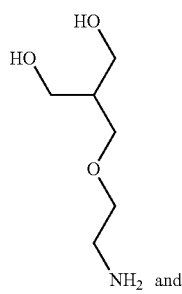

formula 18 and

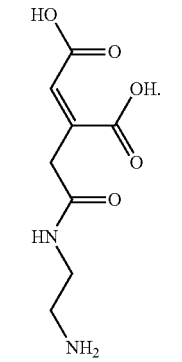

formula 19

In another preferred embodiment for preparing a poly(organo)phosphazene molecule conjugate according to the present invention the pH sensitive linker is protected before step b).

The term "protected" as used herein and unless otherwise defined refers to a group that is added to an oxygen or nitrogen atom to prevent its further reaction during the course of derivatization of other moieties in the molecule in which the oxygen or nitrogen is located. A wide variety of oxygen and nitrogen protecting groups are known to those skilled in the art of organic synthesis. Preferably, the protecting group is selected from the group consisting of allyloxycarbonyl (Aloc), benzyl (Bn), benzyloxycarbonyl (Cbz), benzyloxymethyl (BOM), tert-butoxycarbonyl (Boc), tert-butyldimethylsilyl (TBS), tert-butyldiphenylsilyl (TBDPS), p-methoxybenzyl (PMB), methoxymethyl (MOM), p-methoxyphenyl (PMP), tosyl (Ts), 2-tosylethoxycarbonyl (Tsoc), 2-(trimethylsilyl)ethoxycarbonyl (Teoc), triisopropylsilyl (TIPS), trityl (Tr), fluorenylmethyl carbamate, fmoc, t-butyl carbamate, benzyl carbamate, acetamide, tosylamide, triphenylmethylamine, benzylamine, acetonide, benzylidene acetal, benzoic acid ester, benzoate ester, benzoate, pivalic acid ester, pivalate ester, pivalate, acetic acid ester, acetate ester, acetate, t-butyldiphenylsilyl ether, TBDPS ether, t-butyldimethylsilyl ether, TBDMS ether, benzyl ether, allyl ether, t-butyl ether, tetrahydropyranyl ether, THP ether, methoxymethyl ether, MOM ether, methyl ester, t-Butyl ester, benzyl ester and 2-alkyl-1,3-oxazoline.

In one preferred embodiment of the process of the present invention the protected pH sensitive linkers are selected from the group consisting of formula 20 to 25:

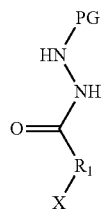

formula 20

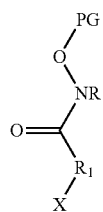

formula 21

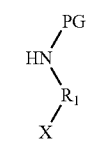

formula 22

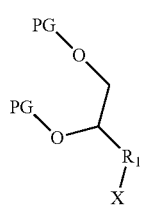

formula 23

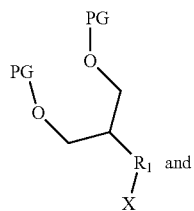

formula 24 and

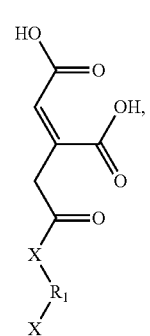

formula 25 wherein PG is a protecting group as defined above.

In one particular preferred embodiment of the process of the present invention the protected pH sensitive linkers are selected from the group consisting of formula 26 to 31

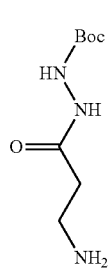

formula 26

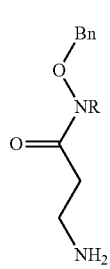

formula 27

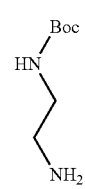

formula 28

-continued

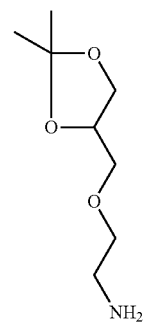
formula 29

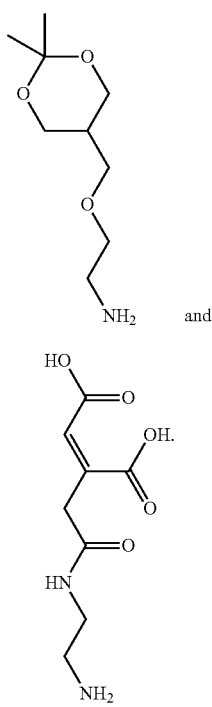
formula 30 and formula 31

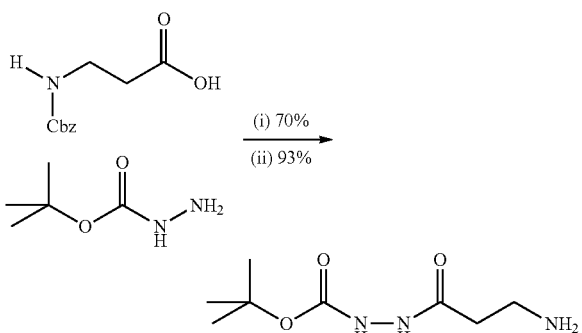

For instance, a hydrazone-containing linker capped with an ethylamine group and a boc protecting group (King, H. D. et al., 1999) could be used for the present invention. Such linker has a free amine group, for reaction with the polymer backbone.

Scheme 3: Synthesis of a boc protected hydrazide linker.

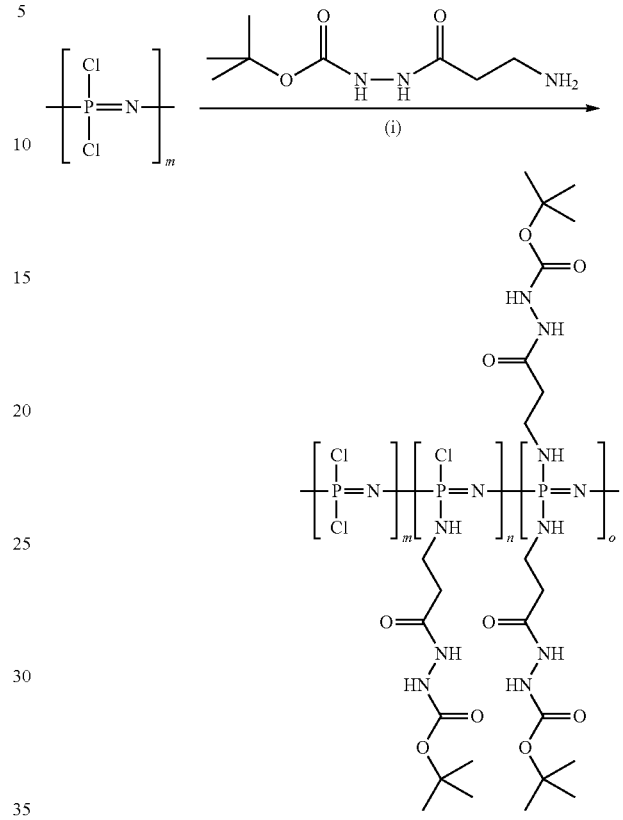

Reagents and conditions: (i) EDCl, CH₂Cl₂, RT, 1.5 h. (ii) H₂, Pd/C (10%), EtOH, RT, 16 h.

The boc-protected hydrazide linker could be then added to the dichloropolyphosphazene.

Scheme 4: Substitution of dichloropolyphosphazene with hydrazide linker.

Reagents and conditions: i) THF, NEt₃, 10-24 h, RT.

Synthesis of any other pH sensitive functional group (as defined above) covalently linked to the polymeric backbone of the poly(organo)phosphazenes of the present invention are described below in the examples.

In another preferred embodiment the process for preparing poly(organo)phosphazenes of the present invention further comprises the step of substitution of at least one chlorine atom with a polyalkylene oxide between steps b) and c).

In one preferred embodiment the process for preparing poly(organo)phosphazenes of the present invention further comprises the step of substitution of at least one chlorine atom with a depsipeptide between steps b) and c).

In another preferred embodiment the process for preparing poly(organo)phosphazenes of the present invention further comprises the step of substitution of at least one chlorine atom with an amino acid alkyl ester between steps b) and c).

In one preferred embodiment the process for preparing poly(organo)phosphazenes of the present invention further comprises the step of substitution of at least one chlorine atom with a tumor targeting ligand between steps b) and c). In this respect any tumor-targeting ligand known in the art and suitable to be covalently bound to polyalkylene oxide oligomers could be used.

In one particular preferred embodiment of the process for preparing poly(organo)phosphazenes according to the present invention, polyethylene glycol oligomers were synthesised with an additional folic acid tumor-targeting ligand in a separate reaction, wherein the diamino polyethylene glycol oligomers were firstly protected on one end. The remaining amino group was then allowed to react with folic acid via a well-reported coupling procedure with EDCl.

Scheme 5: Synthesis of a folic acid-capped amino polyethylene oxide.

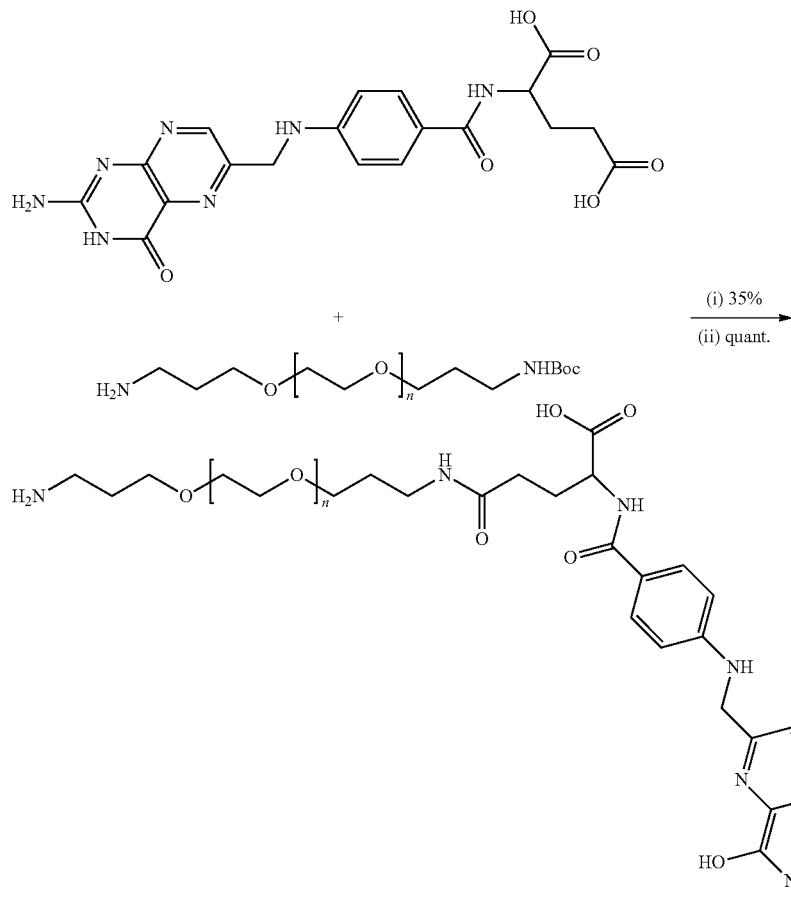

Reagents and conditions; (I) Dioxane, NEt$_3$, RT, 16 h, purification on a Sephadex column ion-exchange chromatography and (ii) CH$_3$COOH, CH$_2$Cl$_2$, RT, 3 h Following simple deprotection in TFA/CH$_2$Cl$_2$, the chosen amount (1-5 mol %) of the boc-protected was then added to the dichloropolyphosphazene, previously substituted with the hydrazide linker. This substitution was allowed to continue to completion (10-24 h) before further steps.

Scheme 6: Partly substituted polyphosphazene with hydrazide linker and folic acid capped PEO oligomer.

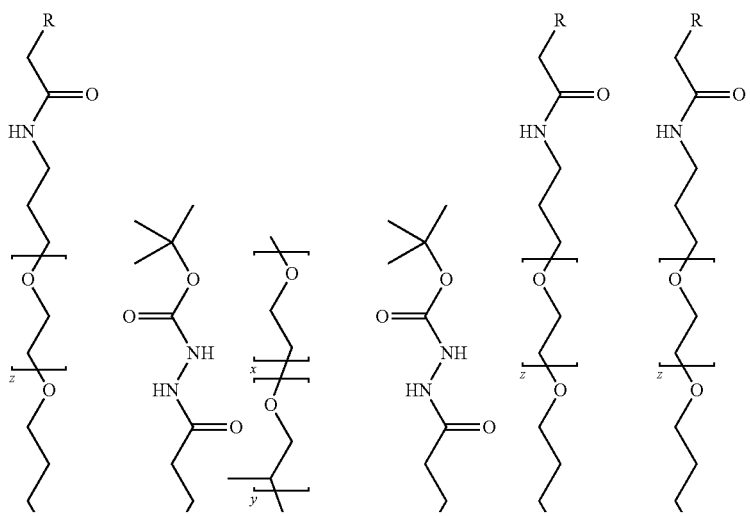

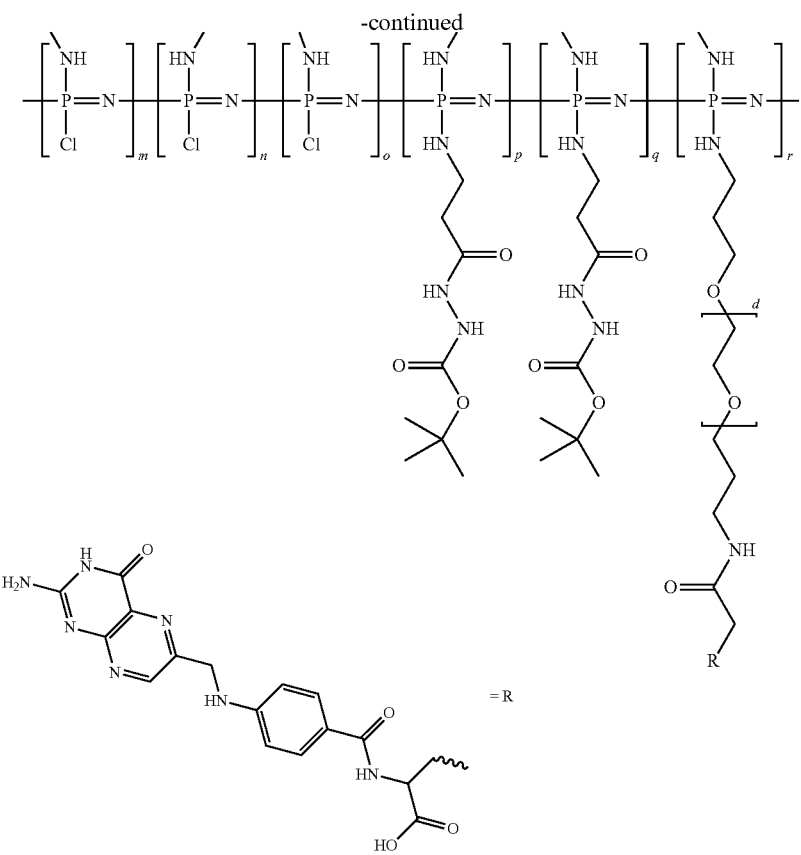

In another preferred embodiment of the process for preparing poly(organo)phosphazenes according to the present invention, chlorine atoms of the polyphosphazenes were substituted in order to enhance the aqueous solubility of the poly(organo)phosphazenes. In this respect any hydrophilic polyalkylene oxide based chain with an amine end group could be used, wherein the length of the chain could be varied. In a particular preferred embodiment of the process for preparing poly(organo)phosphazenes according to the present invention step d) was performed by replacing the remaining chlorine atoms with mono amine-capped polyalkylene oxide oligomers. These mono amine-capped polyalkylene oxide oligomers add water solubility, hydrodynamic volume and number of arms to the polymers (in this respect it should be noted that a large number of arms might also be an important factor for renal clearance). Preferably, amine-capped Jeffamines® are used for this purpose. The excess PEO-PPO-NH$_2$ and remaining salts are then removed by dialysis.

Scheme 7: Completely substituted polyphosphazene with hydrazone linker, folic acid capped PEO oligomer and PEO-PPO side chains.

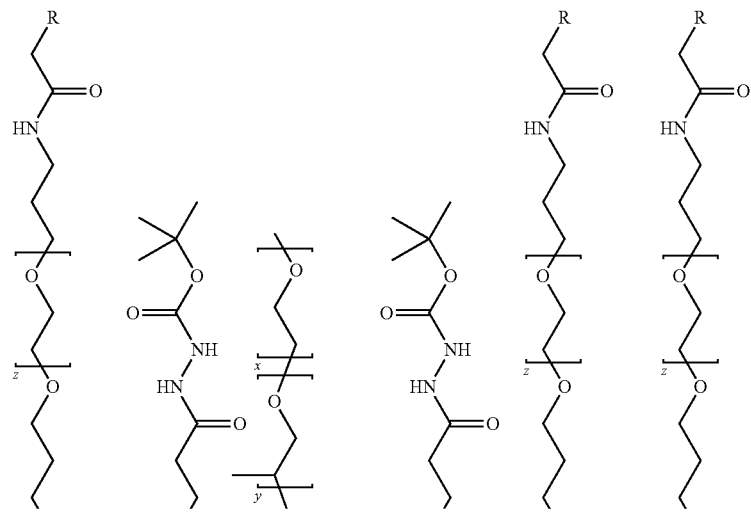

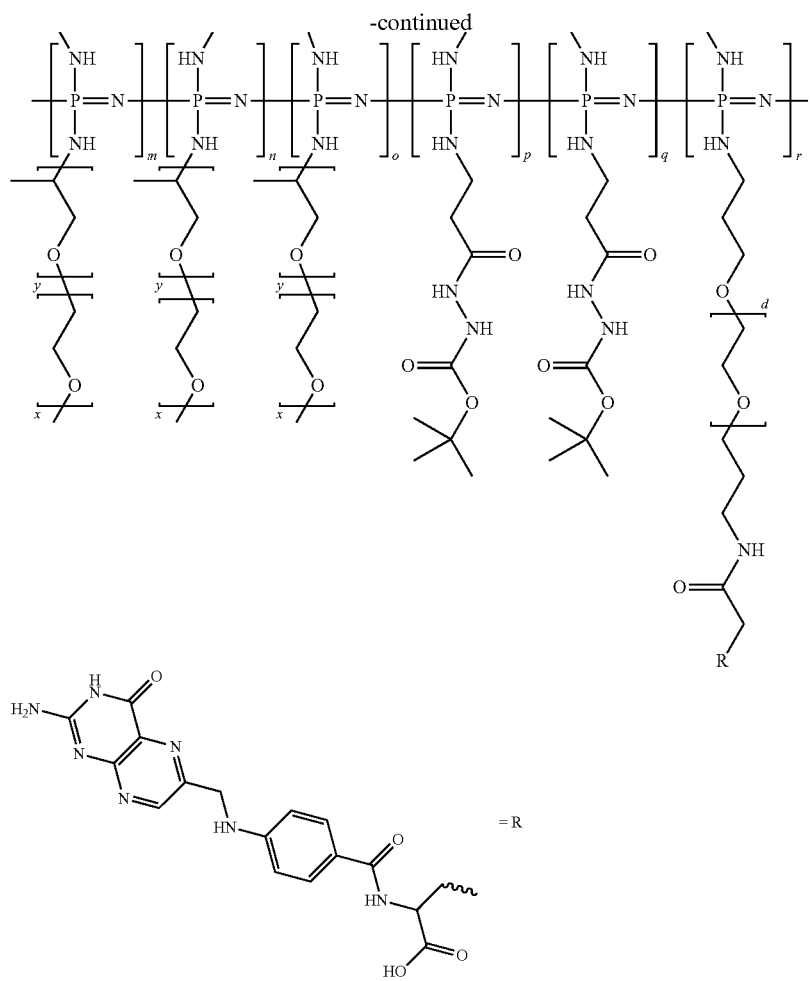

In a third aspect, the present invention relates to the polyorganophosphazene molecule conjugates obtainable by the process according to the present invention.

In a fourth aspect, the present invention relates to the polyorganophosphazene molecule conjugates according to the present invention or to the polyorganophosphazene molecule conjugates obtainable by the process according to the present invention for use in medicine, preferably for use in the treatment of cancer.

In a fifth aspect, the present invention relates to pharmaceutical compositions comprising a polyorganophosphazene molecule conjugate according to present invention or a polyorganophosphazene molecule conjugate obtainable by the process according to the present invention and a pharmaceutically active carrier.

Pharmaceutical compositions as defined herein typically can be formulated by methods known to those skilled in the art preferably utilizing pharmaceutically acceptable components. The term "pharmaceutically acceptable" refers to those properties and/or substances which are acceptable to the patient from a pharmacological/toxicological point of view and to the manufacturing pharmaceutical chemist from a physical/chemical point of view regarding factors such as formulation, stability, patient acceptance and bioavailability.

In this context, a pharmaceutically acceptable carrier and/or vehicle typically includes the liquid or non-liquid basis of the inventive pharmaceutical composition. If the inventive pharmaceutical composition is to be provided in liquid form as it is preferred in the present invention the carrier will be typically pyrogen-free water; isotonic saline or buffered (aqueous) solutions, e.g. phosphate, citrate etc. buffered solutions. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

In another aspect, the present invention concerns a method of treatment of cancer comprising administering a poly(organo)phosphazene according to the present invention. Preferably, the poly(organo)phosphazene according to the present invention is administered into the blood stream, i.e. intravenously.

EXAMPLES

1. General Experimental 1.1. Materials

Figure 1:
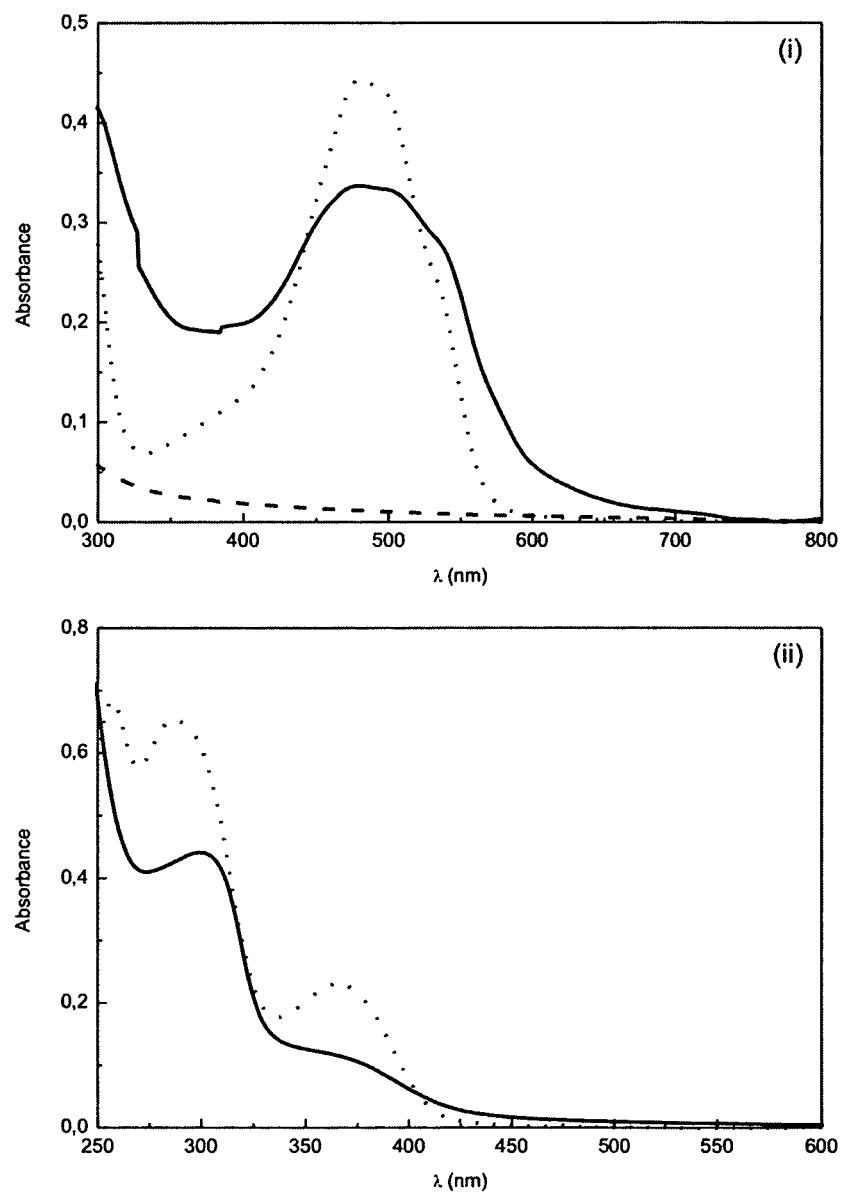
FIG. 1 shows a UV-Vis spectra in $H_2O$ of i) epirubicin (dotted line) and polyphosphazene 1 (dashed line) and polymer 1 loaded with 2 wt % epirubicin hydrochloride (continuous line); ii) folic acid (dotted line) and polymer 5, loaded with 0.5 wt % folic acid.

All solvents were dried using standard laboratory procedures. All synthetic procedures were carried out either in a glove box (MBRAUN) under argon or under nitrogen using standard schlenk line techniques. Epirubicin hydrochloride was purchased from Molekula Deutschland Ltd. (Taufkirchen, Germany). Amine capped polyetheramine copolymers (PEOPPO-NH$_2$), sold under the trademane Jeffamines, were donated by Huntsman Performance Products and used as received. Unless otherwise stated, the PEO-PPO-NH$_2$ had an M$_n$ of 1000 and an ethylene oxide/propylene oxide ratio of 19/3. Where stated that a 2K polyetheramine was used, it had an M$_n$ of 2070 and ethylene oxide/propylene oxide ratio of 10/31. PCl$_5$ was purified by sublimation and stored under argon. Triethylamine was dried over molecular sieves and distilled prior to use. All other chemicals were purchased from Sigma Aldrich and used without prior purification. All glassware was dried in an oven overnight prior to use.

1.2. Measurements

Characterisation by NMR spectroscopy was conducted on Bruker 200 MHz spectrometer using CDCl$_3$, DMSO-d$^6$ or D$_2$O, as reported. $^{31}$P NMR was conducted using 85% phosphoric acid as an external standard. UV-Vis spectra were carried out on a Perkin Elmer Lambda 25 UV/VIS spectrophotometer. Gel permeation chromatography was carried out on a Viscotek HT-GPC instrument using two PLgel mixed bead columns assembled in series and a refractive index detector. Molecular weights were estimated from Viscothek Polycal polystyrene standards. Samples were eluted at 35° C. with THF containing 0.1% (w/w) tetra-n-butyl ammonium nitrate. FTIR spectra were measured with a Perkin Elmer Spectrum 100 FTIR spectrometer. A 1290 Infinity UPLC system (Agilent Technologies, Vienna, Austria) equipped with a diode array detector and a Zorbax Eclipse Plus C18 column (2.1 mm×50 mm, 1.8 µm particle size) was used for kinetic studies of the drug release. The samples were eluted at a flow rate of 0.5 mL/min at room temperature with a mobile phase composition of 25% acetonitrile in water (v/v) containing 0.1% formic acid (v/v) in isocratic mode. UV detection was carried out at 254 nm in the linear range of the detector.

1.3. Synthesis of Monomer Cl$_3$PNTMS (Honeyman, C. H. Et al., 1994)

40 g LiN(SiMe$_3$)$_2$ (239 mmol) were dissolved in 800 mL diethylether. The reaction was then cooled to 0° C. and stirred for 30 min. 20.91 mL PCl$_5$ (239 mmol) were then added dropwise at 0° C. The solution was allowed to warm to room temperature and stirred for 2.5 hours. After cooling to 0° C. again, 19.35 mL SO$_2$Cl$_2$ (239 mmol) were added and the mixture was stirred for another 3 hours at 0° C. The reaction was filtered through Celite and the volatiles removed under vacuum. The product was purified by vacuum distillation (50° C., 4 mbar) to yield chlorophosphoranimine as a colourless, viscous oil. The product was stored under inert argon atmosphere at −40° C. Yield 35%; $^{1}$H NMR (CDCl$_3$): δ=0.15 (s, 9H) ppm, $^{31}$P NMR (CDCl$_3$); −54.1 ppm.

1.4. Synthesis of β-Alanyl-Boc-Hydrazide

The boc-protected linker, β-alanyl-boc-hydrazide was synthesised similar to literature procedures (King, H. D. et al., 1999). β-Ala-OH (5.00 g, 22.4 mmol), boc-NH—NH$_2$ (2.96 g, 22.4 mmol) and N-(3-dimethylaminopropyl)-N ethylcarbodiimide hydrochloride (EDCl) (4.51 g, 23.51 mmol) were dissolved in 200 mL DCM and stirred for 2 hours at room temperature. The reaction mixture was extracted with 200 mL of 0.1 M acetic acid. The aqueous layer was extracted three times with 50 mL DCM. The organic layers were then combined and extracted twice with 200 mL 0.1 M acetic acid, twice with 200 mL of saturated aqueous sodium hydrogencarbonate and once with 200 mL H$_2$O. The organic layer was dried over MgSO$_4$, solvents removed under vacuum and the product then further dried under high vacuum to yield β-alanyl-boc-hydrazide as a white powder. Alanyl-boc-hydrazide (5.01 g, 14.86 mmol) was hydrogenated at 3 bar in 150 mL methanol with 10% Pd—C (0.3 g) for 24 hours. The reaction was filtered through Celite and rotary evaporated. The product was dried under high vacuum to yield β-Alanyl-BOChydrazide as white foam. Yield 65%, FTIR (solid) vmax/cm$^{-1}$=3260br (N—H), 2867w (C—H), 1670s (C=O). $^1$H-NMR (CDCl$_3$): δ=1.46 (s, 9H), 2.50 (m, 2H), 3.13 (m, 2H), 5.30 (b, 4H) ppm.

1.5. Synthesis of Pegylated Folic Acid

Di-tert-butyl carbonate (0.9 g, 0.66 mmol) was added dropwise to a solution of o,o'-bis(3-aminopropyl)polyethylene glycol (144 mg, 0.6 mmol) in dioxane (20 mL) and triethylamine (73 mg, 0.7 mmol). The mixture was the stirred at room temperature for 16 hours. The solvent was removed under vacuum, the product dissolved in CH$_2$Cl$_2$ and reprecipitated into diethylether/hexane at −15° C. The white solid was filtered and used for the next step. A portion of the product (320 mg) and EDCl (45 mg, 234 mmol) were added to a flask and placed under nitrogen. In a separate vessel, folic acid (103 mg, 234 mmol) was dissolved with heating in DMF 25 mL. The solution was returned to room temperature and added to the reaction mixture. The mixture was stirred for 12 h at room temperature. The DMF was removed under high vacuum and the product purified in a Sephadex column, eluted with 0.1 M NaHCO$_3$. The product was then deprotected in a 2:1 CH$_2$Cl$_2$:CF$_3$COOH solution and stirred for 3 hours at room temperature after which the solvent was removed under high vacuum. Overall yield 35%. $^1$H-NMR (d$^6$-dmso): δ=1.69 (m, 4H), 1.92 (b, 2H), 2.12 (b, 2H), 2.74 (t, 4H), 3.141 (m, 2H), 3.85 (m, 2H), 4.08 (m, 1H), 4.43 (b, 2H), 6.63 (d, 2H), 6.83 (s, 2H), 6.59 (d, 2H), 7.93 (s, 1H) 8.57 (s, 1H) ppm. UV-Vis λmax (0.1M NaOH)/nm 228, 262 and 302 (ε/dm$^3$ mol$^{-1}$ cm$^{-1}$26900, 21500 and 11500).

1.6. Polymer Synthesis

1.6.1. General Polymer Synthesis Procedure

Polymers were synthesised according to Allcocks' procedure for the living cationic polymerisation of chlorophosphoranimine (Allock, H. R. et al., 1996). The following example procedure describes the procedure used for the synthesis of polymer 1. Other polymers were synthesised accordingly, with the ratio of monomer to initiator varied and the relative amounts of substituents adjusted in order to obtain polymers desired polymers.

In the glove box, initiator PCl$_5$ (18.55 mg, 0.09 mmol) and monomer Cl$_3$PNTMS (0.51 g, 2.26 mmol) were dissolved in CH$_2$Cl$_2$ (5 mL) at room temperature. The solution was stirred for 12 h and the solvent removed under vacuum. The resulting polydichlorophosphazene was then dissolved in anhydrous THF in an inert atmosphere. 0.2 equivalent of the hydrazide linker (0.18 g, 0.91 mmol) and NEt$_3$ (0.09 g, 0.91 mmol) were then added to the polymer solution and allowed to react for 24 hours. An excess of PEO-PPO-NH$_2$ (2.4 eq, 10.86 g, 10.86 mmol) was then added to the reaction mixture and allowed to react for a further 24 hours. The solvent was then removed under vacuum and resulting polymers were purified by dialysis (12 kDa cut-off) for 48 hours against deionized H$_2$O followed by 24 hours against MeOH. The solvent was removed under a stream on nitrogen and the polymers were dried under vacuum to give waxy solids or highly viscous liquids in yields of 50-60%. All polymers were analysed by GPC analysis, $^{31}$P NMR, $^1$H NMR and FTIR spectroscopy. All other polymers were synthesized using this procedure with the exception that polymers 5-6 were synthesised via the sequential addition of 0.25 eq linker, 0.01 eq FA-PEO-NH$_2$ and then an excess (2.74 eq) PEO-PPO-NH$_2$ and that polymers 7-9 were synthesised with 0.2 eq linker, followed by the desired amount of PEO-PPO-NH$_2$ and then an excess of ethyl glycinate ester, with 24 hours reaction time allowed between each addition.

1.6.1.1. Characterisation Data for Polymers 1-4

Scheme 8: Structure of poly(organo)phosphazenes 1-4, incorporating a protected hydrazide linker and hydrophilic polyalkylene oxide side chains.

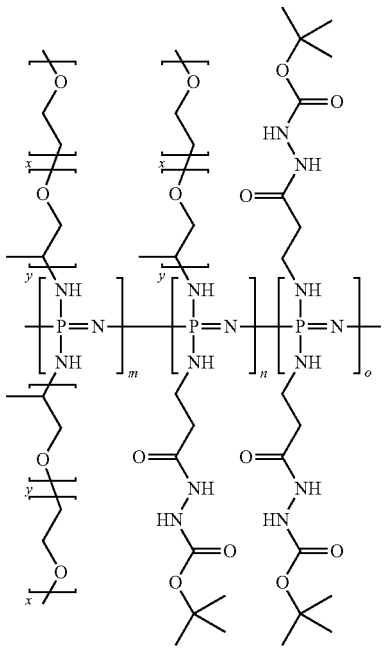

Polymer 1: M:I 25:1, Linker:PEO-PPO 1:2; FTIR (solid) vmax/cm$^{-1}$=3277 (N—H), 2881 (C—H), 1740 (C=O), 1688 (C=O) and 1106 (P=N); $^1$H-NMR (CDCl$_3$): δ=1.12 (br, 14H), 1.43 (s, 9H), 3.37 (s, 6H), 3.64 (m, 170H); $^{31}$P NMR (CDCl$_3$): δ=−1.5 (ppm). GPC (g mol$^{-1}$) M$_n$=32360, M$_w$=41188.

Polymer 2: M:I 25:1, Linker:PEO-PPO 1:1.7; FTIR (solid) vmax/cm$^{-1}$=3268 (N—H), 2865 (C—H), 1735 (C=O), 1687 (C=O) and 1104 (P=N). $^1$H-NMR (CDCl$_3$): δ=1.13 (d, 16H), 1.47 (s, 9H), 3.38 (s, 6H), 3.64 (m, 144H). $^{31}$P NMR (CDCl$_3$): δ=−0.7 (ppm). GPC (g mol$^{-1}$) M$_n$=31319, M$_w$=46172.

Polymer 3: M:I 25:1, Linker:PEO-PPO 1:0.1; FTIR (solid) vmax/cm$^{-1}$=3269 (N—H), 2872 (C—H), 1722 (C=O), 1672 (C=O) and 1093 (P=N). $^1$H-NMR (CDCl$_3$): δ=1.13 (d, 1H) 1.46 (s, 9H), 3.38 (m, 0.3H), 3.65 (s, 9H). $^{31}$P NMR (CDCl$_3$): δ (ppm). GPC (g mol$^{-1}$) M$_n$=13968, M$_w$=18220.

Polymer 4: M:I 25:1, Linker:PEO-PPO 1:1 (2070 M$_n$ PEO-PPO-NH$_2$ side chains); FTIR (solid) vmax/cm$^{-1}$=3259 (N—H), 2863 (C—H), 1727 (C=O), 1646 (C=O) and 1101 (P=N). $^1$H-NMR (CDCl$_3$): δ=1.15 (d, 30H) 1.49 (s, 9H), 3.62 (b, 124H). $^{31}$P NMR (CDCl$_3$): δ (ppm). GPC (g mol$^{-1}$) M$_n$=48954, M$_w$=63799.

1.6.1.2. Characterisation Data for Polymers 5 and 6

Scheme 9: Structure of poly(organo)phosphazenes 5-6, incorporating a protected hydrazide linker, a folic acid targeting moiety and hydrophilic polyalkylene oxide side chains.

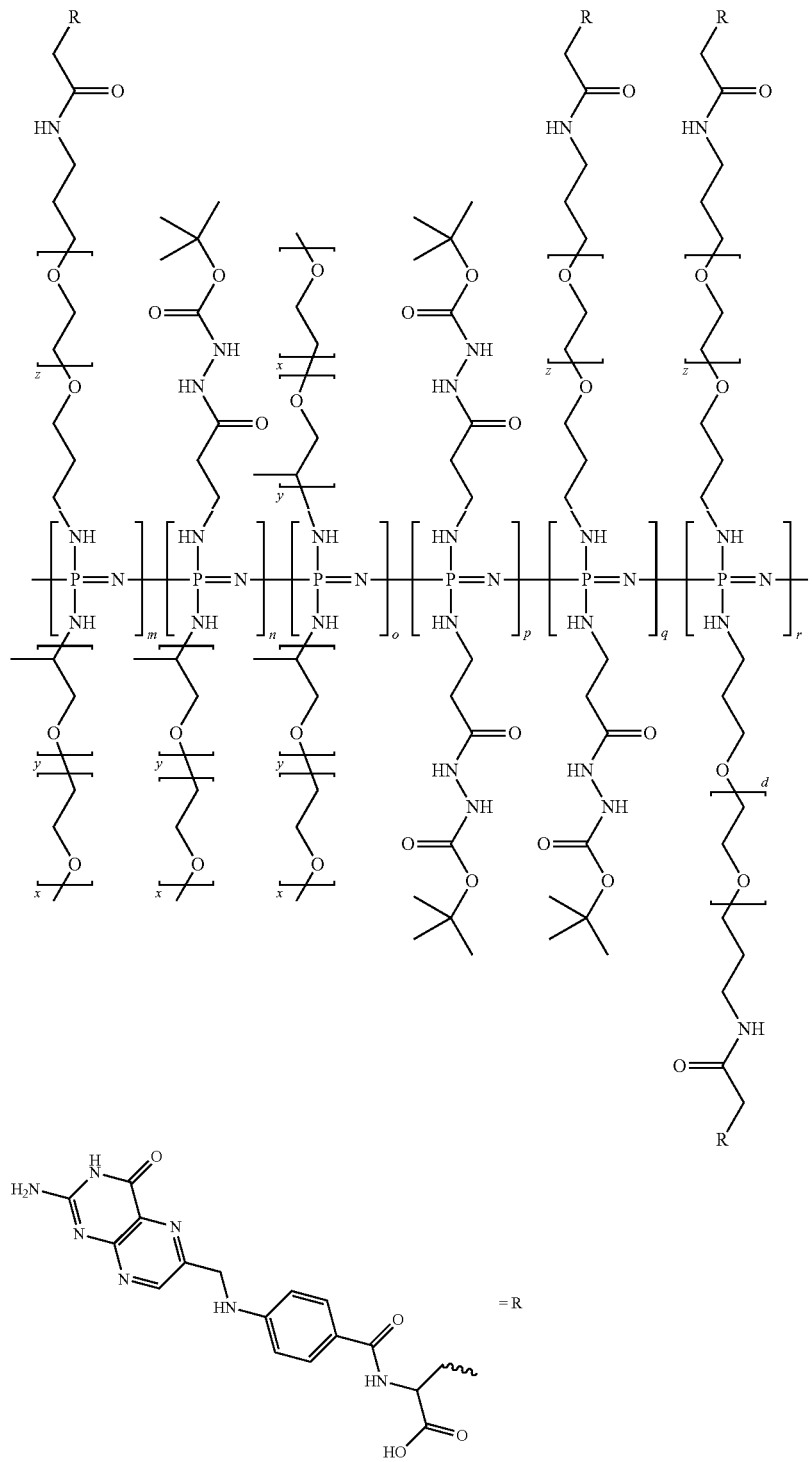

Polymer 5: UV-Vis λmax (H$_2$O)/nm 256, 283 and 368 (ε/dm$^3$ mol$^{-1}$ cm$^{-1}$ 26900, 25100 and 9120). FTIR (solid) vmax/cm$^{-1}$=3289 (N—H), 2882 (C—H), 1653 (C=O), and 1107 (P=N). $^1$H-NMR (CDCl$_3$): δ=1.11 (d, 15H), 1.41 (s, 9H), 3.35 (6H), 3.61 (s, 178H). $^{31}$P NMR (CDCl$_3$): δ=−0.8 (ppm). GPC (g mol$^{-1}$) M$_n$=53200, M$_w$=159800.

Polymer 6: UV-Vis λmax (H$_2$O)/nm 256, 283 and 368 (ε/dm$^3$ mol$^{-1}$ cm$^{-1}$ 26900, 25100 and 9120); FTIR (solid)

vmax/cm$^{-1}$=3289 (N—H), 2882 (C—H), 1653 (C=O), and 1107 (P=N). $^1$H-NMR (CDCl$_3$): δ=1.12 (m, 12H), 1.46 (s, 9H), 3.35 (m, 6H), 5.30 (b, 160H). $^{31}$P NMR (CDCl$_3$): δ=−0.8 (ppm). GPC (g mol$^{-1}$) $M_n$=33225, $M_w$=81393.

1.6.1.3. Characterisation Data for Polymers 7-9

Scheme 10: Structure of poly(organo)phosphazenes 7-9, incorporating a combination of protected hydrazide linker, ethyl glycinate and polyalkylene oxide side chains.

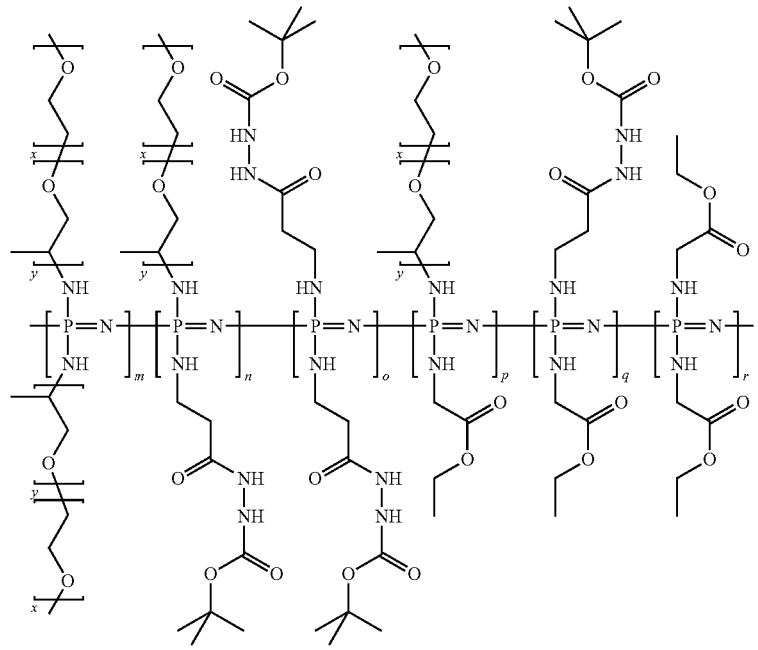

Polymer 7: M:I 1:50, Linker:PEO-PPO:Ethyl glycinate 1:1.3:2; FTIR (solid) vmax/cm$^{-1}$=3281 (N—H), 2866 (C—H), 1739 (C=O), 1691 (C=O), and 1108 (P=N). $^1$H-NMR (500 MHz, CDCl$_3$): δ=1.14 (d, br, 9.2H), 1.26 (br, 6.4H), 1.45 (s, 9H), 3.38 (s, 4H), 3.65 (br, 108H). $^{31}$P NMR (CDCl$_3$): δ (ppm) −0.3. GPC (g mol$^{-1}$) $M_n$=63197, $M_w$=100688.

Polymer 8: M:I 1:50, Linker:PEO-PPO:Ethyl glycinate 1:1.4:1.7; FTIR (solid) vmax/cm$^{-1}$=3280 (N—H), 2866 (C—H), 1739 (C=O), 1691 (C=O), and 1107vs (P=N). $^1$H-NMR (200 MHz, CDCl$_3$): δ=1.12 (d, br, 10H), 1.26 (t, 4.5H), 1.44 (s, 9H), 3.38 (s, 5H), 3.65 (br, 120H). $^{31}$P NMR (CDCl$_3$): δ (ppm) −0.6. GPC (g mol$^{-1}$) $M_n$=75681, $M_w$=104429.

Polymer 9: M:I 1:50, Linker:PEO-PPO:Ethyl glycinate 1:1.4:1.3; FTIR (solid) vmax/cm$^{-1}$=3292 (N—H), 2867 (C—H), 1793 (C=O), 1683 (C=O), and 1104 (P=N). $^1$H-NMR (200 MHz, CDCl$_3$): δ=1.12 (d, br, 12H), 1.26 (t, 4.2H), 1.44 (s, 9H), 3.38 (s, 4H), 3.65 (br, 120H). $^{31}$P NMR (CDCl$_3$): δ (ppm) 0.8. GPC (g mol$^{-1}$) $M_n$=68467, $M_w$=103219.

1.7. Drug Loading

A sample of the protected polymer (150 mg) was dissolved in a 2:1 CH$_2$Cl$_2$: CF$_3$COOH solution and stirred for 3 hours. The solvent was then removed under high vacuum. The deprotected polymer was then added to anhydrous methanol (10 mL) and 1 equivalent per hydrazide group of epirubicin hydrochloride. The mixture was stirred under reflux for 24 hours. The product was then purified by dialysis against methanol for 5 days. The amount of epirubicin hydrochloride covalently bound to the polymers was measured in H$_2$O by UV-Vis spectroscopy from the absorbance at 481 nm (E=11200) (Erdinc, N. et al., 2004).

1.8. Drug Release

The release of the anticancer drug from the hydrazone-linked poly(phosphazene) epirubicin conjugates was carried out at 37° C. in aqueous buffers in the dark. An incubator was used to control the temperature of the sample solutions during the release experiments. In order to simulate the pH-value of tumor and healthy tissue the polymer-drug conjugates were incubated in aqueous buffer solutions at pH 5 (0.1 M sodium acetate) and pH 7.2 (0.1 M phosphate), respectively. The sample vials were only removed from the incubator for the short time of the analysis with UPLC (ultra performance liquid chromatography). A 1290 Infinity UPLC system (Agilent Technologies, Vienna, Austria) equipped with a diode array detector and a Zorbax Eclipse Plus C18 column (2.1 mm×50 mm, 1.8 μm particle size) was used for kinetic studies of the drug release. The samples were eluted at a flow rate of 0.5 ml/min at room temperature with a mobile phase composition of 25% acetonitrile in water (v/v) containing 0.1% formic acid (v/v) in isocratic mode. UV detection was carried out at 254 nm in the linear range of the detector. Injections of 1 μl were performed in regular time intervals after addition of the buffer solution to the PPZ-EPI conjugates (2.5 mg/ml) and the amount of EPI released from the PPZ was determined. For this purpose the calibration was carried out with the pure substance epirubicin hydrochloride in acetate buffer (0.1 M, pH 5) in a concentration range from 1 μg/ml to 50 μg/ml. The linear response of the detector was confirmed by a correlation coefficient >0.99. Thus the peak areas allowed calculation of the concentration of free EPI in the sample solutions.

1.9. Polymer Degradation Studies

Polymer samples (0.20 g) were dissolved in a pH 7.4 phosphate buffer (5 mL) and incubated at 37° C. An aliquot (0.25 mL) was then removed at regular intervals and the solvent was evaporated. The polymer was then dissolved in THF, filtered through a 45 μm PTFE filter and analysed by GPC with an RI detector.

2. Synthesizing of Different Poly(Organo)Phosphazenes (Polymers 1-9) According to the Present Invention

2.1. Synthesizing of Comb-Branched Poly(Organo)Phosphazenes

Dichloropolyphosphazenes were synthesised by the polymerisation of chlorophosphoranime according to scheme 2. This simple room temperature polymerisation results in hydrolytically unstable polymers with narrow polydispersities. The chlorine atoms were then substituted with the required amount of boc-protected hydrazide linker (scheme 11).

Scheme 11: Synthesis of polymers 1-4, hydrophilic polyphosphazene copolymers with a boc-protected hydrazide linker and hydrophilic polyalkylene oxide side chains.

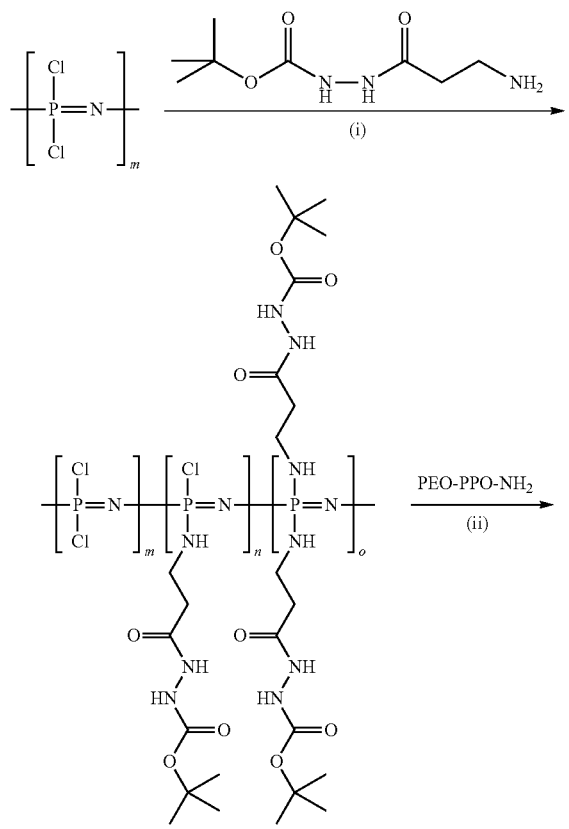

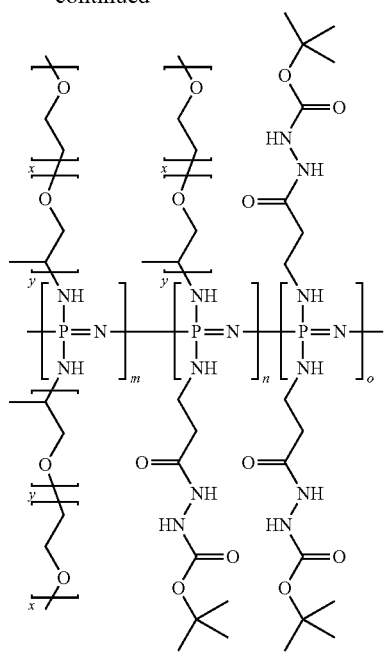

Reagents and conditions: (i) and (ii) THF, NEt₃ RT, 24 h.

This substitution was allowed to continue to completion before addition of an excess of the hydrophilic, amine capped polyoxyalkylene copolymer (PEO-PPO-NH$_2$), thus replacing the remaining chlorine atoms to give a series polymers with excellent aqueous solubility (with the exception of polymer 3, with only 5% PEO-PPO side chains. The structures confirmed by $^1$H, $^{31}$P NMR and FTIR spectroscopy. $^{31}$P NMR analysis showed that all Cl atoms have been substituted with only one broad peak being observed due to the mixed geminal substitution pattern (Hindenlang, M. D. et al., 2010). $^1$H NMR spectrsocopy was therefore used to calculate the relative ratios of the two substituents (table 1) by integration of the doublet associated with the PPO methyl groups at 1.1 ppm versus the boc groups belonging to the hydrazide linker at 1.4 ppm. GPC analysis was used to estimate the molecular weights of the polymers (table 1). The molecular weights of the polymers could be carefully controlled by varying the initial ratio of initiator to monomer and the susbsequent substituents. The measured molecular weights measured by GPC calibrated against linear polystyrene standards were a factor of 2-3 lower than that estimated by the initiator:monomer ratio, with the factor greater for polymers with a higher molecular weight. This deferred elution time being attributed to the branched, closely packed nature of the polymers, leading to a lower hydrodynamic volume in comparison to the linear standards Kaskhedikar, N. et al., 2006). The polydispersities Mw/Mn were measured to be 1.2-1.4. The slightly higher usual range for these polymers (1-1.3) (Allock, H. R. et al., 1997) and is thought to be a consequence of the mixed substitution of the side chains, which would be expected to produce a statistical distribution of substituents.

TABLE 1

| Polymer | M:I | Linker/PEO-PPO ratio[a] | $M_{n\,(calc)}$/kg mol$^{-1}$ | $M_n{}^c$/kg mol$^{-1}$ | $M_w/M_n$ |
|---|---|---|---|---|---|
| 1 | 25:1 | 1:2 | 80 | 32 | 1.27 |
| 2 | 25:1 | 1:1.7 | 83 | 31 | 1.47 |
| 3 | 25:1 | 1:0.1 | 27 | 14 | 1.30 |
| 4* | 25:1 | 1:1 | 159 | 49 | 1.30 |
| 5 | 50:1 | 1:2 | 160 | 53 | 1.25 |
| 6 | 25:1 | 1:2 | 81 | 34 | 1.28 |

[a]Measured by $^1$H NMR;
[b]Calculated from the initial monomer:initiator and side group ratios;
[c]Measured by GPC analysis and calibrated against linear polystyrene standards;
*Synthesised with 2070 $M_n$ PEO-PPO-NH$_2$ side chains

2.2. Conjugation of Folic Acid

Polymers 5 and 6 were also synthesized with an additional folic acid tumor-targeting ligand. The folate receptor has been shown to be over-expressed in many human cancers (Lu, Y. J. et al., 2002) and its conjugation to macromolecular carriers has been successfully implemented by a number of authors (Lu, Y. J. et al., 2002, Zhang, Y. Q. et al., 2010; Pan, D. et al., 2003, Zhang, Y. H. et al., 2010). FA-PEO-NH$_2$ ($M_n \approx 1940$) was synthesised via coupling of the γ-carboxylic acid group to a mono boc-protected diamine. Following deprotection, the FA-PEO-NH$_2$ was added, in small amounts (<1%), to the polymer chains in a sequential substitution reaction as described earlier. UV-Vis spectroscopy was used to confirm the incorporation of folic acid moieties in the polymers (FIG. 1). Observed 0.5 wt % of the 5 pegylated folic acid gives an average of 1-2 folic acid moieties per macromolecule.

2.3. Loading of Epirubicin

The boc protected hydrazide groups on the polymers were deprotected with CF$_3$COOH and the resulting amine groups allowed to react with carbonyl group in the side chain of the anti-cancer drug epirubicin (a stereoisomer doxorubicin) (scheme 12).

Scheme 12: Simplified structure for hydrophilic poly(organo)phosphazenes loaded with epirubicin and folic acid moieties.

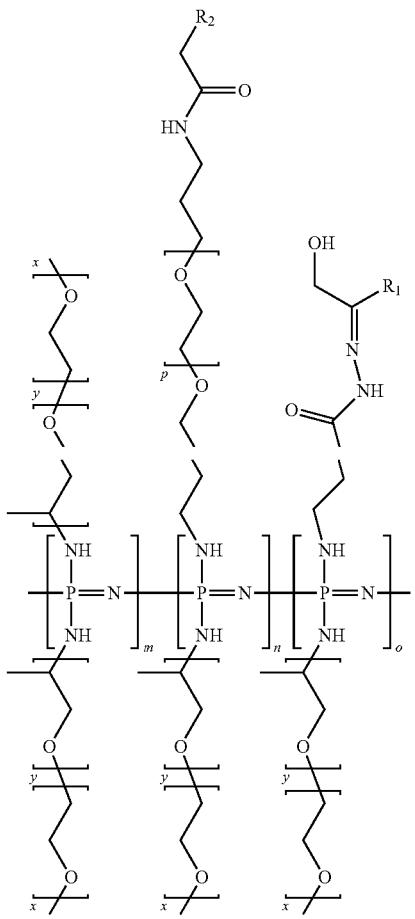

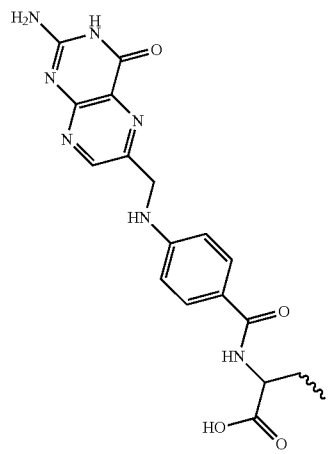 = R₂

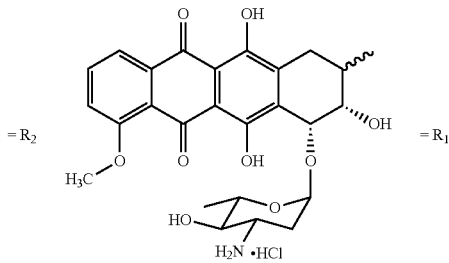 = R₁

The polymer-drug conjugates were then purified by dialysis for several days against methanol. Successful loading of the drug was confirmed, and the % loading calculated, by UV-Vis analysis (FIG. 1) from the absorbance at 481 nm. Loading was, however, lower than expected (≈2-3%), with only approximately 10% of the total available hydrazide groups bearing drug moeities. Further reactions, in which the epirubicin-polymer solution was heated to reflux did improve the loading and enabled the preparation of polymers with a loading of up to 7%, which corresponds to approximately 40% of the total hydrazide moieties.

2.4. pH Controlled Release of Epirubicin

Figure 2:
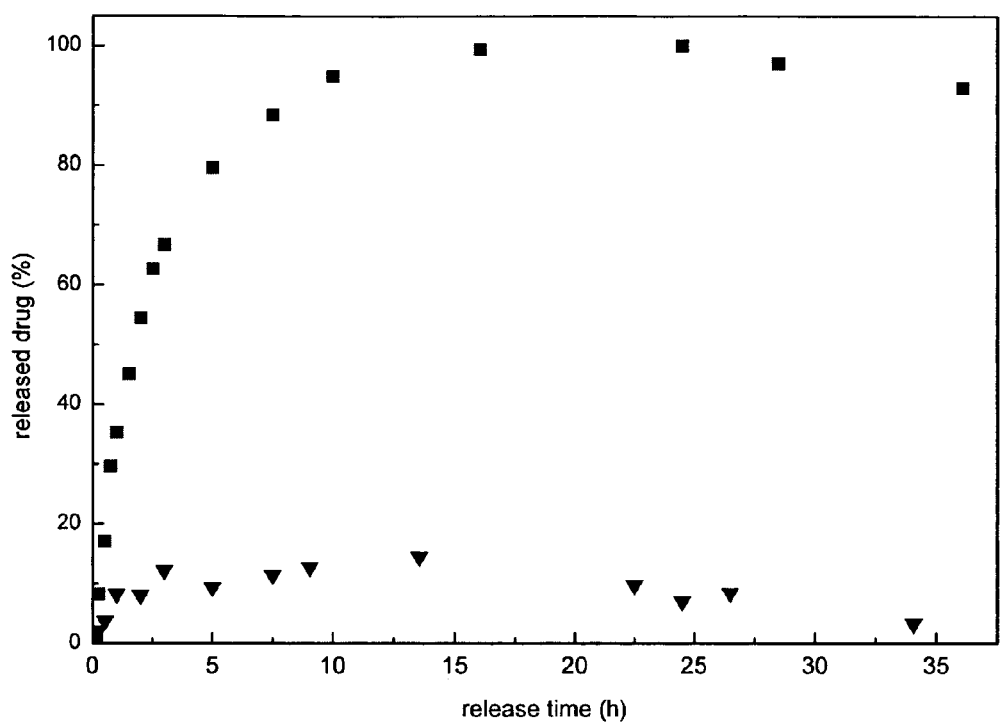
FIG. 2 shows the release of epirubicin from the hydrazide-linked polyphosphazene at 37° C. in acidic environment ■ (acetate buffer, pH 5), and a neutral solution ▼ (pH 7.4, phosphate buffer). The amount of the released epirubicin was estimated using a calibration curve for the free drug.

The release of epirubicin from the polymer-drug conjugates was then analysed by HPLC under simulated physiological conditions at 37° C. in a pH 7.4 phosphate buffer and in an acidic medium at pH 5 in an acetate buffer solution (FIG. 2). At pH 5 a steady release of the drug molecule from the polymer was observed, with 100% release from the polymer-drug conjugate being observed within 15 hours. Meanwhile, only minimal release was observed within a period of 24 h from the polymers at pH 7.4. The rate of release is comparable to reports from authors using similar hydrazide based polymer systems (Lee, C. C. et al., 2006; Prabaharan, M. et al., 2009).

2.5 Biodegradability

Figure 3:
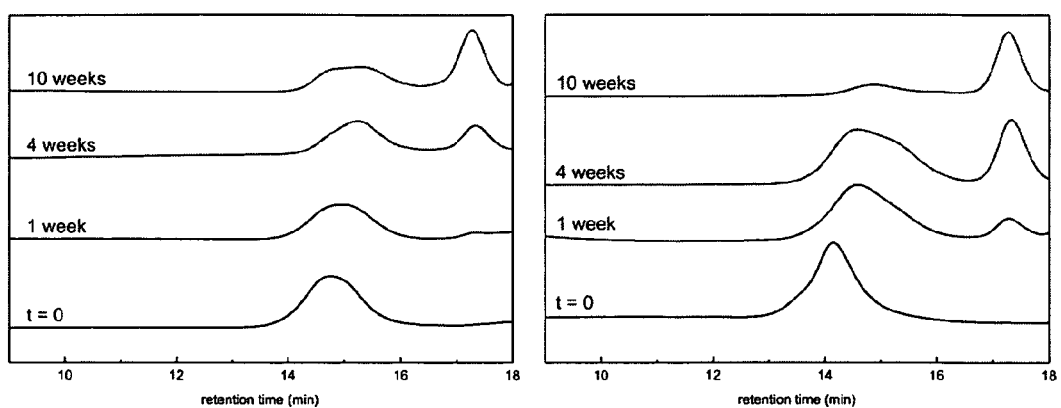
FIG. 3 shows GPC chromatographs showing the degradation of polymer 2 (left) and polymer 7 (right) at 37° C. in an aqueous buffer solution (pH 7.4). Broadening and decrease in intensity and a shift to longer retention time of the polymer peak is observed alongside an increase in the peak associated with the polyalkylene oxide side chains as they are eliminated from the polymer. Polymer 7, incorporating 25% ethyl glycinate side groups, degrades considerably faster than for polymer 2, with no amino acid ester side groups.
Figure 4:
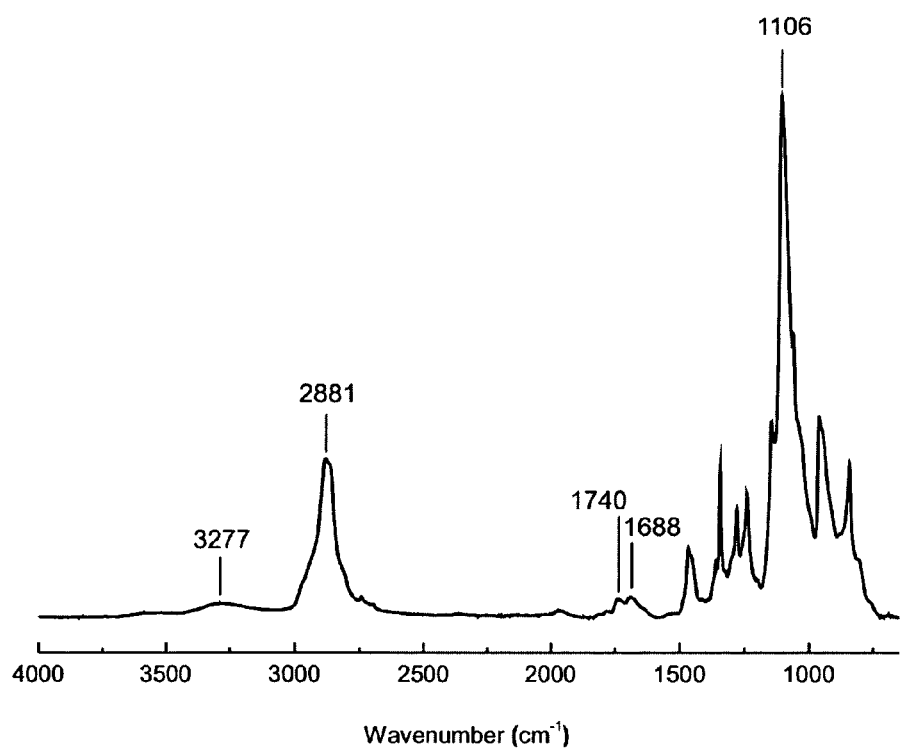
FIG. 4 shows an ATR-FTIR spectrum of polymer 1. Significant bands include the P=N stretching band of the polyphosphazene main chain at 1104 cm$^{-1}$, the C=O bands stemming from the hydrazone linker, a relatively large C—H band, predominantly from the polyalkylene oxide side chains at 2867 cm$^{-1}$ and the NH bands at 3292 cm$^{-1}$ and 3500 cm$^{-1}$.
Figure 5:
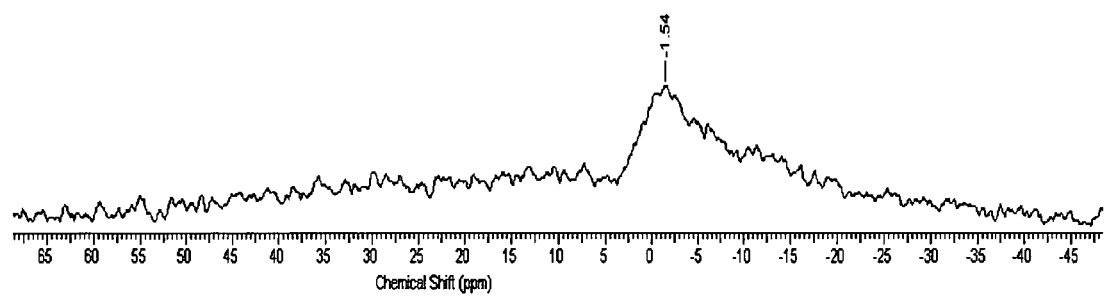
FIG. 5 shows a $^{31}$P NMR of polymer 1. A single broad peak is observed due to the mixed substitution of the phosphazene backbone.
Figure 6:
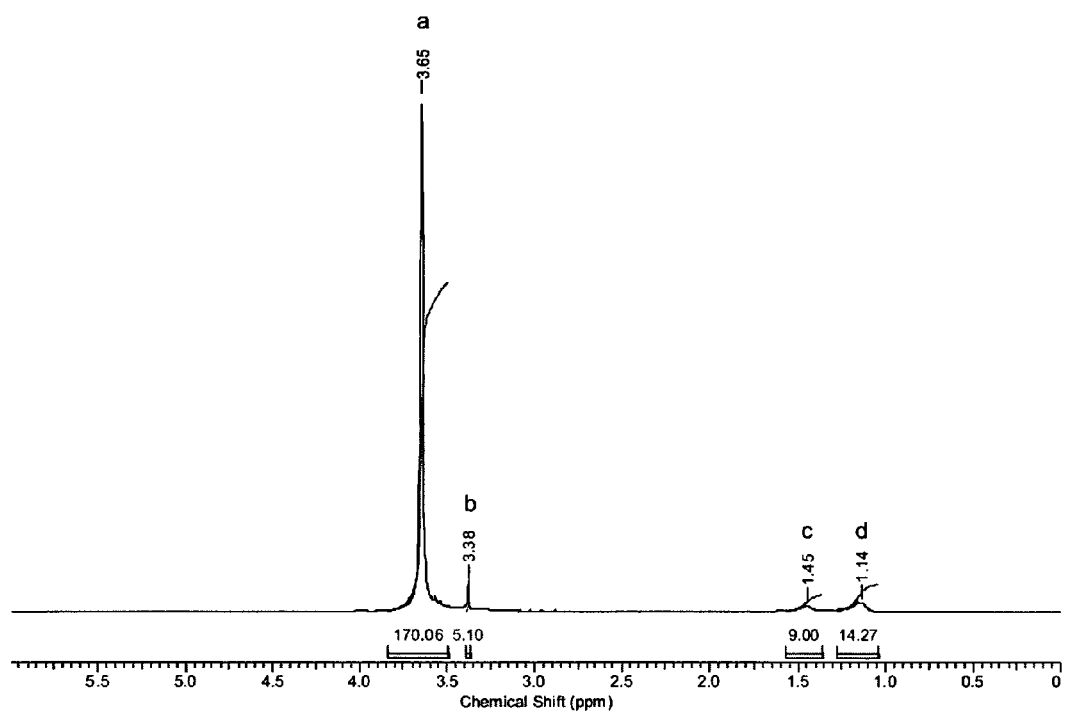
FIG. 6 shows a $^{1}$H NMR of polymer 1 showing: a) Polyalkylene oxide $CH_2$ protons, b) —$OCH_3$ end groups c) Boc protecting group of the hydrazone linker and d) $CH_3$— groups from the PPO groups of the polyalkylene oxide side chains.
Figure 7:
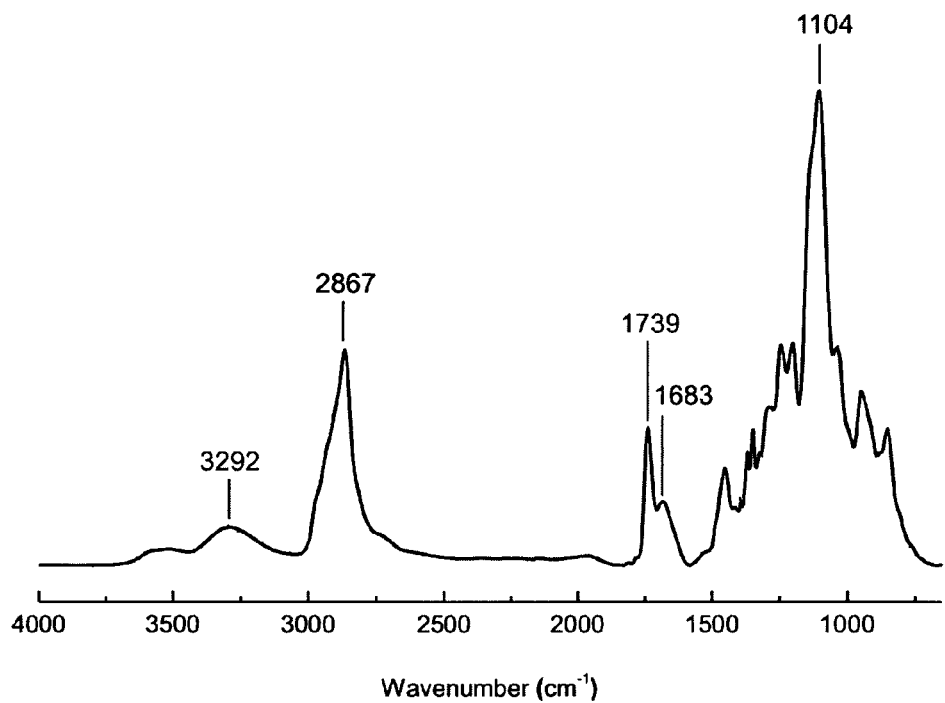
FIG. 7 shows an ATR-FTIR spectrum of polymer 7. Relevant bands include the P=N stretching band of the polyphosphazene main chain at 1104 cm$^{-1}$, the C=O bands stemming from both the linker and the ethyl glycinate side groups, a relatively large C—H band, predominantly from the polyalkylene oxide side chains at 2867 cm$^{-1}$ and the NH bands at 3292 cm$^{-1}$ and 3500 cm$^{-1}$.
Figure 8:
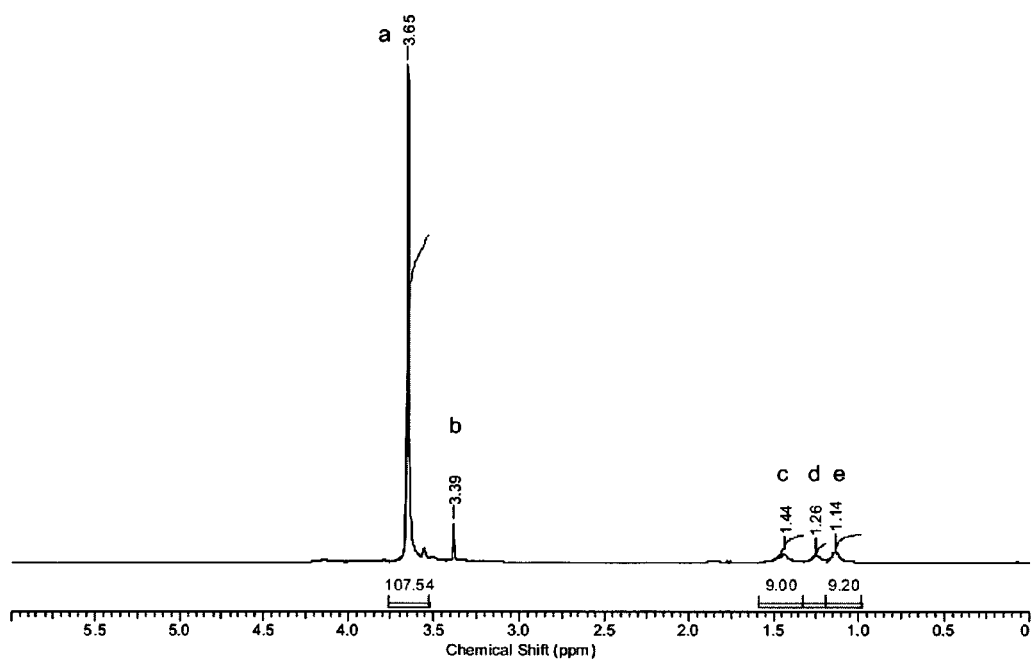
FIG. 8 shows a $^{1}$H NMR spectrum of polymer 7 showing: a) Polyalkylene oxide $CH_2$ protons, b) —$OCH_3$ end groups c) boc protecting group of the hydrazone linker d) $CH_3$ groups of the ethyl glycinate groups and e) $CH_3$— groups from the PPO groups of the polyalkylene oxide side chains.
Figure 9:
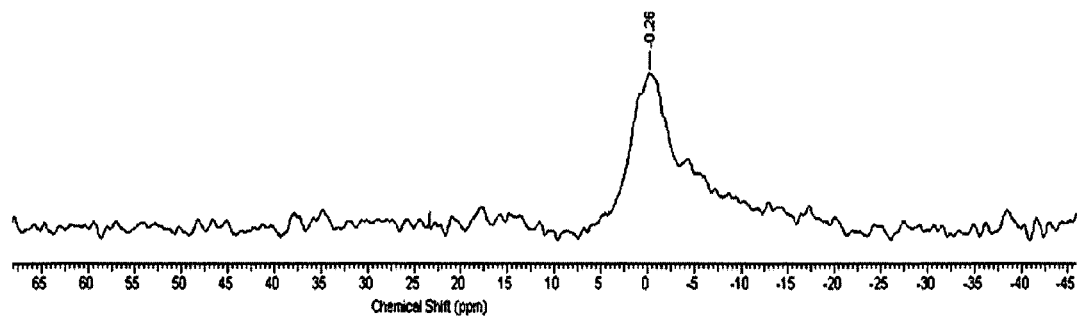
FIG. 9 shows a $^{31}$P NMR of polymer 7. A single broad peak is observed due to the mixed substitution of the phosphazene backbone.

The biodegradability of a selection of these polymers was tested at 37° C. at pH 7.4 and at pH 5 and monitored by size exclusion chromatography. No significant degradation is observed during the time-frame of the drug release (0-24 hours), making these polymers viable candidates for the intended application of drug-delivery. The polymers did, however, undergo degradation over longer periods under these simulated physiological conditions (FIG. 3). A clear broadening and a shift to longer retention time of the polymer peak is observed. Furthermore, a peak in the GPC chromatographs was observed to appear at a later retention time. This peak, which increases in relative intensity over time, corresponds to an Mn≈1000, strongly suggesting that the polyalkyleneoxide side chains are first ejected from the polymers. This supports previous studies which suggest that the mechanism for degradation of amino substituted polyphosphazenes involves removal of the side groups to form hydroxyphosphazenes and phosphazenes, which then undergo rapid hydrolytic chain cleavage (Allock, H. R. et al., 1977). It has been reported that the rate of degradation of polyphosphazenes can be altered significantly by careful choice of substituents. In particular, the incorporation of amino acid side chains has been shown to considerably decrease the hydrolytic stability of hydrophilic poly(organo)phosphazenes (Vandorpe and Schacht, 1996; Andrianov and Marin, 2006). To this end, a series of polymers via sequential addition of Linker were synthesized, PEO-PPO-NH₂ and then ethyl glycinate ester side chains in varying ratios (table 2).

TABLE 2

| Polymer | Ratio of substituents[a] | | | $M_n^c$/kg | |
| | Linker | PEO-PPO | Ethyl glycinate | mol⁻¹ | $M_w/M_n$ |
|---|---|---|---|---|---|
| 7 | 1 | 1.3 | 2 | 63 | 1.6 |
| 8 | 1 | 1.4 | 1.7 | 76 | 1.4 |
| 9 | 1 | 1.4 | 1.3 | 68 | 1.5 |

[a]Determined by ¹H NMR Monomer:initiator ratio used 1:50

The polymers all showed good water solubility but the incorporation of a third different side chain led to a small increase in the polydispersity. As shown in FIG. 3, the degradation is considerably accelerated upon incorporation of ethyl glycinate side groups. After 2 weeks, the Mn of polymer 7, in which around 47% of the chlorine atoms were substituted with ethyl glycinate groups, was reduced to 66% of its original value, whereby polymer 2 had an Mn value 80% of its original. The effect of polymer molecular weight, of steric crowding, as well as the different ratios of polyalkylene oxide and amino acid ester groups render a direct correlation for the rate of degradation for all polymers difficult and the precise impact of these relationships requires further investigation (Vandorpe and Schacht, 1996) in order to attain a better understanding and hence ability to truly tailor the precise required rate of degradability.

Conclusions

These results demonstrate the potential of polyphosphazenes to create defined and tunable macromolecules for the targeted delivery of anti-cancer drugs. The present invention describes the synthesis of hydrophilic, biodegradable polyphosphazenes via the living polymerisation procedure. The polymers can be readily decorated with a combination of targeting ligands and drug molecules. In addition, the present invention demonstrates the pH triggered release of an anti-cancer drug from the polymer drug conjugates, as well as the tailoring of the biodegradability by incorporation of amino acid ester side groups. Thus, the polymers represent of the present invention extremely promising candidates for the targeted delivery of anti-cancer drugs.

3. Examples of Binding Anti-Cancer Drugs to Polyphosphazenes Via a Hydrazide Linker Below are two examples of how anti-cancer drugs that do not already possess an available carbonyl or amine (for acontityl linker) functionality could also be bound to the polymers.

3.1. Binding of Cisplatin to Poly(Organo)Phosphazene According to the Present Invention The cisplatin pro-drug of formula 32 is formed by a simple reaction of the well known compound Pt (IV)Cl$_2$(OH)$_2$ (NH$_3$)$_2$ with an anhydride (Aryal, Hu et al.). The platinum IV pro-drug would be rapidly reduced to upon release to platinum II and hence would release the actual free drug cisplatin and not the conjugate.

formula 32

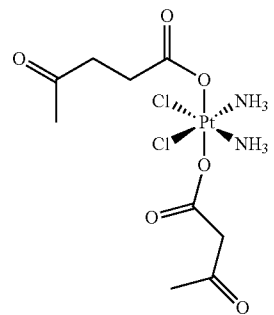

Cisplatin prodrug (Aryal, Hu et al.)

formula 33

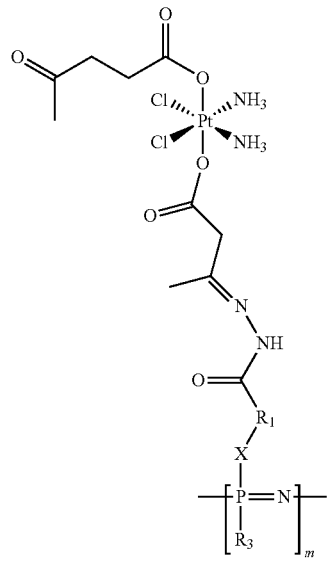

Cisplatin pro-drug bound to a polyphosphazene via the acid-labile hydrazone linker

3.2. Binding of Paclitaxel to Poly(Organo)Phosphazene According to the Present Invention A second example involves the synthesis of a prodrug of Paclitaxel LEV-PTX as reported in the literature (Alani, Bae et al.). LEV-PTX (formula 34, centre) would allow the simple coupling of this common anti-cancer drug to our polyphosphazene system via the carbonyl group at position 4.

formula 34

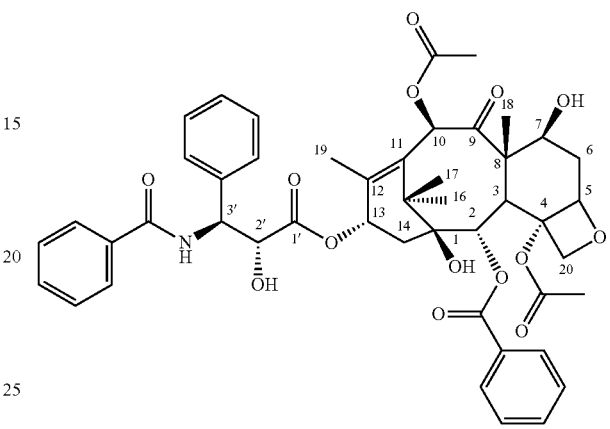

PTX

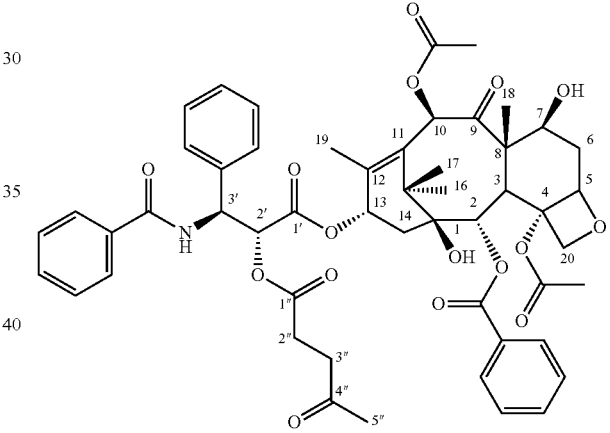

LEV-PTX

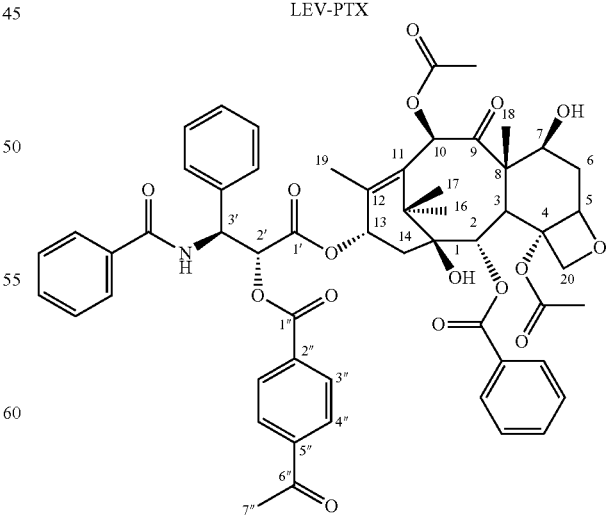

4AB-PTX

Paclitaxel pro-drugs (Image taken from (Alani, Bae et al.)

4. Synthesis of Poly(Organo)Phosphazenes Covalently Binding pH Sensitive Linkers

4.1. Imine Linker

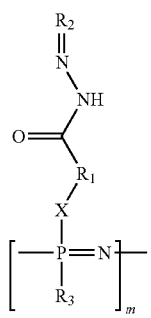

formula 2

Polyphosphazene bound imine linker

An imine linker can be realised by reaction of the readily available n-boc ethylenediamine with chloropolyphosphazene in an analogous reaction to that described for the hydrazide linker above. Following deprotection, the amine bond can react with a carbonyl functionality of a given drug compound. The imine bond hydrolyses much slower than the hydrazide bond and is therefore less preferable.

Scheme 13: Synthetic procedure for the synthesis of an imine forming linker

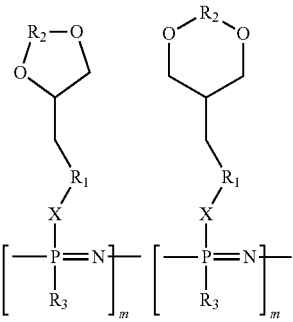

4.2. Acetal Linkers formula 5 and 6

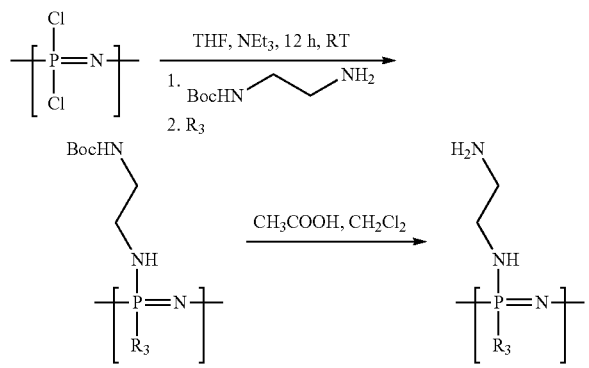

Synthetic procedure for the synthesis of an acetal forming linker

Starting with 3-aminopropane-1,2-diol or 4-aminobutane-1,3-diol for the 5 or 6 membered cyclic acetal respectively. Protection of the diol as cyclic acetal groups using standard procedures gives an amino functionalised compound which can be used as a substituent for the polyphosphazene substitution reaction. The diol functionalised polymer can then react with the carbonyl group of the desired drug compound to form a pH labile bond between the polyphosphazene and the drug compound.

Scheme 14: Synthetic procedure for the synthesis of an acetal forming linker

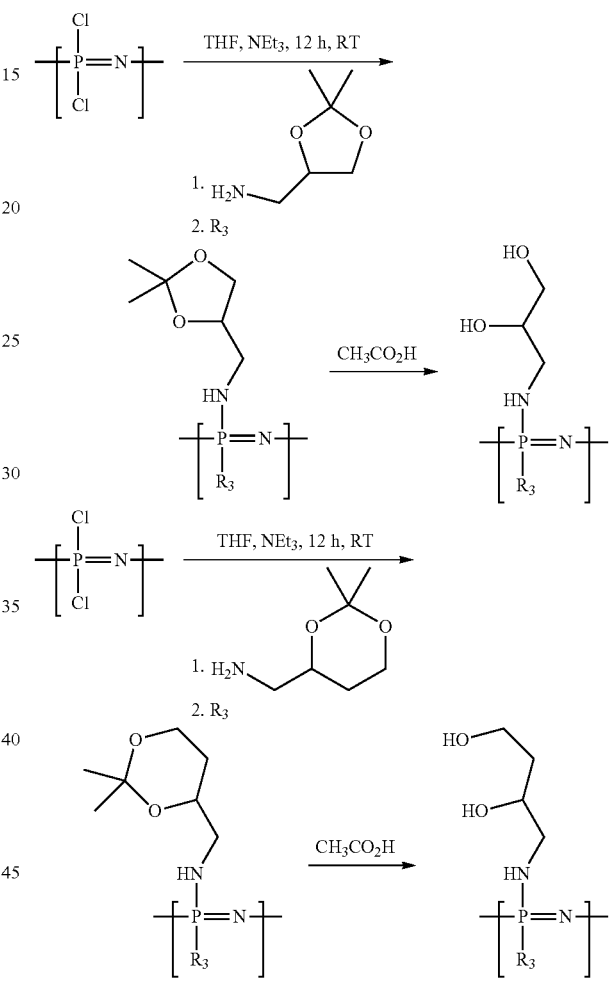

4.3. Hydroxamate Linker formula 3

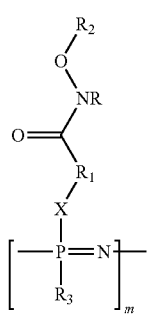

Polyphosphazene bound hydroxamate linker

A hydroxamate linker can be easily synthesised using standard synthetic procedures. Readily available benzyl protected alanine can be reacted with the chloropolyphosphazene using the general procedure reported in the patent. The polymer would then be completely substituted with polyalkylene oxide chains as reported in the patent. Following simple deprotection and activation with an N-hydroxysuccinimide group (NHS) using standard synthetic procedures, the polymer is reacted with N-methylhydroxylamine hydrochloride or hydroxylamine as per (Kenawy, El-Newehy et al. 2007), to give the hydroxamate linker. This linker can bind to any carboxylate group of a given anti-cancer drug.

Scheme 14: Synthetic procedure for the synthesis of an acotinyl forming linker

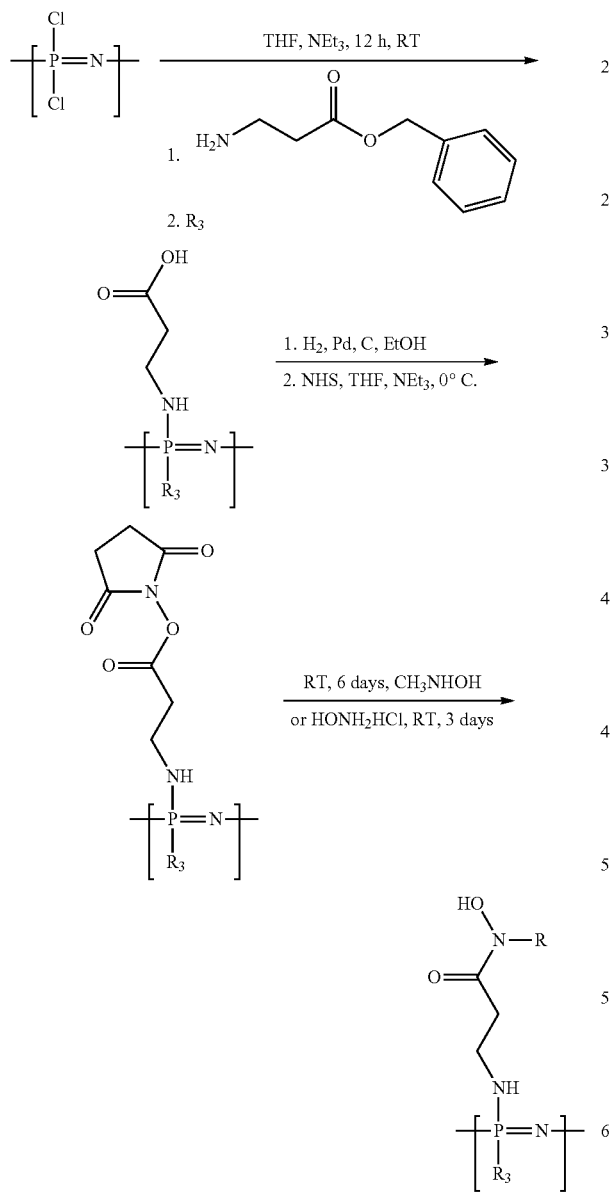

4.4. Acotinyl Linkers

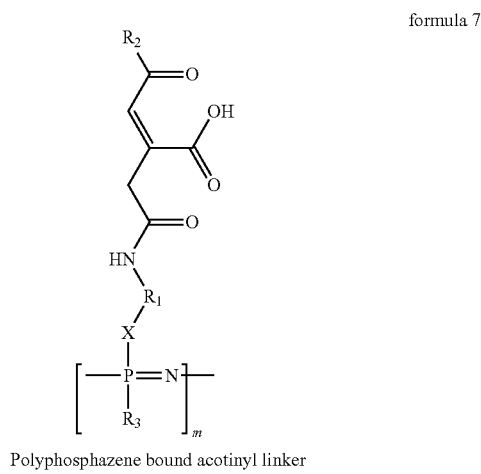

formula 7

Polyphosphazene bound acotinyl linker

Aconitic anhydride reacts with n-boc ethylenediamine (Yoo, Lee et al. 2002). This product can then be used for the substitution of chloropolyphosphazene. The carboxylic acid group can be used to couple anti-cancer drugs via an amine group.

Scheme 15: Synthetic procedure for the synthesis of an acotinyl forming linker

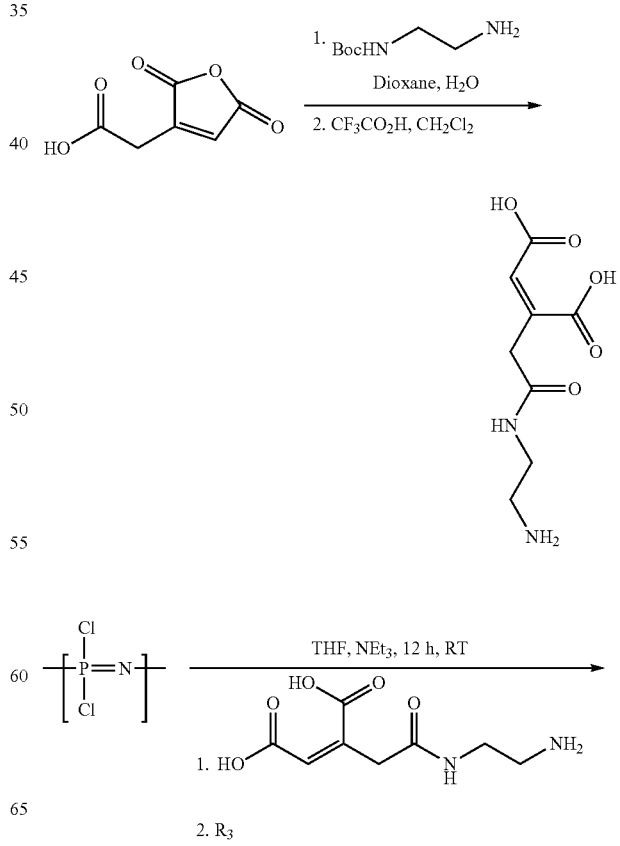

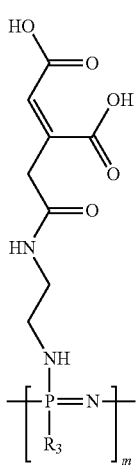

LITERATURE

S. F. El-Amin, M. S. Kwon, T. Starnes, H. R. Allcock and C. T. Laurencin, *J. Inorg. Organomet. Polym. Mater.*, 2006, 16, 387-396.

H. R. Allcock, in *Chasin, M. and R. Langer*, Editon edn., 1990, pp. 163-194.

V. Blackstone, A. J. Lough, M. Murray and I. Manners, *Journal of the American Chemical Society*, 2009, 131, 3658-3667.

H. R. Allcock, C. A. Crane, C. T. Morrissey, J. M. Nelson, S. D. Reeves, C. H. Honeyman and I. Manners, *Macromolecules*, 1996, 29, 7740-7747.

J. M. Nelson, A. P. Primrose, T. J. Hartle, H. R. Allcock and I. Manners, *Macromolecules*, 1998, 31, 947-949.

K. Matyjaszewski, M. K. Moore and M. L. White, *Macromolecules*, 1993, 26, 6741-6748.

J. M. Nelson and H. R. Allcock, *Macromolecules*, 1997, 30, 1854-75 1856.

S. Y. Cho and H. R. Allcock, *Macromolecules*, 2007, 40, 3115-3121.

H. R. Allcock, T. J. Fuller, D. P. Mack, K. Matsumura and K. M. Smeltz, *Macromolecules*, 1977, 10, 824-830.

S. E. M. Ibim, A. M. A. Ambrosio, M. S. Kwon, S. F. El-Amin, H. R. Allcock and C. T. Laurencin, *Biomaterials*, 1997, 18, 1565-1569.

H. R. Allcock, S. R. Pucher and A. G. Scopelianos, *Biomaterials*, 1994, 15, 563-569.

J. Vandorpe and E. Schacht, *Polymer*, 1996, 37, 3141-3145.

H. R. Allcock, S. R. Pucher and A. G. Scopelianos, *Macromolecules*, 1994, 27, 1071-1075.

A. Singh, N. R. Krogman, S. Sethuraman, L. S, Nair, J. L. Sturgeon, P. W. Brown, C. T. Laurencin and H. R. Allcock, *Biomacromolecules*, 2006, 7, 914-918.

S. Sethuraman, L. S, Nair, S. El-Amin, R. Farrar, M. T. N. Nguyen, A. Singh, H. R. Allcock, Y. E. Greish, P. W. Brown and C. T. Laurencin, *J. Biomed. Mater. Res. Part A*, 2006, 77A, 679-687.

J. H. L. Crommen, E. H. Schacht and E. H. G. Mense, *Biomaterials*, 95 1992, 13, 511-520.

J. H. L. Crommen, E. H. Schacht and E. H. G. Mense, *Biomaterials*, 1992, 13, 601-611.

S. M. Ibim, A. A. Ambrosio, D. Larrier, H. R. Allcock and C. T. Laurencin, *Journal of Controlled Release*, 1996, 40, 31-39.

S. Sethuraman, L. S, Nair, S. El-Amin, M. T. Nguyen, A. Singh, N. Krogman, Y. E. Greish, H. R. Allcock, P. W. Brown and C. T. Laurencin, *Acta Biomater.*, 6, 1931-1937.

L. S, Nair and C. T. Laurencin, *Prog. Polym. Sci.*, 2007, 32, 762-798.

A. K. Andrianov, A. Marin and B. E. Roberts, *Biomacromolecules*, 2005, 6, 1375-1379.

A. K. Andrianov, *J. Inorg. Organomet. Polym. Mater.*, 2006, 16, 397-406.

J. Luten, M. J. van Steenbergen, M. C. Lok, A. M. 5 de Graaff, C. F. van Nostrum, H. Talsma and W. E. Hennink, *European Journal of Pharmaceutical Sciences*, 2008, 33, 241-251.

M. D. Hindenlang, A. A. Soudakov, G. H. Imler, C. T. Laurencin, L. S, Nair and A. H. R., *Polymer Chemistry*, 2010, Advance article DOI 10.1039/C1030PY00126K.

S. Lakshmi, D. S. Katti and C. T. Laurencin, *Advanced Drug Delivery Reviews*, 2003, 55, 467-482.

C. Chun, S. M. Lee, C. W. Kim, K. Y. Hong, S. Y. Kim, H. K. Yang and S. C. Song, *Biomaterials*, 2009, 30, 4752-4762.

G. D. Kang, S. H. Cheon and S. C. Song, *International Journal of Pharmaceutics*, 2006, 319, 29-36.

J. Y. Seong, Y. J. Jun, B. M. Kim, Y. M. Park and Y. S. Sohn, *International Journal of Pharmaceutics*, 2006, 314, 90-96.

J. X. Zhang, L. Y. Qiu, Y. Jin and K. J. Zhu, *J. Biomed. Mater. Res. 20 Part A*, 2006, 76A, 773-780.

L. Y. Qiu and M. Q. Yan, *Acta Biomater.*, 2009, 5, 2132-2141.

Y. S. Sohn, H. Baek, Y. H. Cho, Y. A. Lee, O. S. Jung, C. O. Lee and Y. S. Kim, *International Journal of Pharmaceutics*, 1997, 153, 79-91.

R. Song, Y. J. Jun, J. I. Kim, C. Jin and Y. S. Sohn, *Journal of Controlled Release*, 2005, 105, 142-150.

F. Greco and M. J. Vicent, *Advanced Drug Delivery Reviews*, 2009, 61, 1203-1213.

R. Haag and F. Kratz, *Angewandte Chemie-International Edition*, 30 2006, 45, 1198-1215.

C. C. Lee, E. R. Gillies, M. E. Fox, S. J. Guillaudeu, J. M. J. Frechet, E. E. Dy and F. C. Szoka, *Proc. Natl. Acad. Sci. U.S.A.*, 2006, 103, 16649-16654.

T. Lammers, V. Subr, K. Ulbrich, W. E. Hennink, G. Storm and F. Kiessling, *Nano Today*, 2010, 5, 197-212.

M. E. Fox, F. C. Szoka and J. M. J. Frechet, *Accounts of Chemical Research*, 2009, 42, 1141-1151.

H. Maeda, J. Wu, T. Sawa, Y. Matsumura and K. Hori, *Journal of Controlled Release*, 2000, 65, 271-284.

Y. J. Lu and P. S. Low, *Advanced Drug Delivery Reviews*, 2002, 54, 675-693.

E. R. Gillies and J. M. J. Frechet, *Pure and Applied Chemistry*, 2004, 76, 1295-1307.

R. Tong and J. J. Cheng, *Polymer Reviews*, 2007, 47, 345-381.

T. Etrych, P. Chytil, M. Jelinkova, B. Rihova and K. Ulbrich, *Macromolecular Bioscience*, 2002, 2, 43-52.

M. Shin, H. Matsunaga and K. Fujiwara, *Histochem Cell Biol*, 133, 677-682.

C. H. Honeyman, A. J. Lough and I. Manners, *Inorg. Chem.*, 1994, 50 33, 2988-2993.

H. D. King, D. Yurgaitis, D. Willner, R. A. Firestone, M. B. Yang, S. J. Lasch, K. E. Hellstrom and P. A. Trail, *Bioconjugate Chemistry*, 1999, 10, 279-288.

N. Erdinc, S. Gokturk and W. Tuncay, *Journal of Pharmaceutical Sciences*, 2004, 93, 1566-1576.

N. Kaskhedikar, J. Paulsdorf, M. Burjanadze, Y. Karatas, D. Wilmer, B. Roling and H. D. Wiemhofer, *Solid State Ionics*, 2006, 177, 703-707.

H. R. Allcock, S. D. Reeves, J. M. Nelson, C. A. Crane and I. Manners, *Macromolecules*, 1997, 30, 2213-2215.

Y. Q. Zhang, Y. H. Sun, X. P. Xu, X. Z. Zhang, H. Zhu, L. L. Huang, Y. J. Qi and Y. M. Shen, *Journal of Medicinal Chemistry*, 2010, 53, 3262-3272.

D. Pan, J. L. Turner and K. L. Wooley, *Chemical Communications*, 65 2003, 2400-2401.

Y. H. Zhang, T. P. Thomas, A. Desai, H. Zong, P. R. Leroueil, I. J. Majoros and J. R. Baker, *Bioconjugate Chemistry*, 2010, 21, 489-495.

M. Prabaharan, J. J. Grailer, S. Pilla, D. A. Steeber and S. Q. Gong, *Biomaterials*, 2009, 30, 5757-5766.

A. K. Andrianov and A. Marin, *Biomacromolecules*, 2006, 7, 1581-1586.

Gillies, E. R. and J. M. J. Fréchet, *Pure and Applied Chemistry*, 2004, 76 (7-8): 1295-1307.

Kenawy, E. R., M. El-Newehy, et al. *Biomacromolecules*, 2007, 8: 196-201.

Lee, C. C., J. A. MacKay, et al. *Nature Biotechnology*, 2005, 23(12): 1517-1526.

Yoo, H. S., E. A. Lee, et al. *Journal of Controlled Release*, 2002, 82(1): 17-27.

What is claimed is:

1. A poly(organo)phosphazene molecule conjugate represented by formula 1,

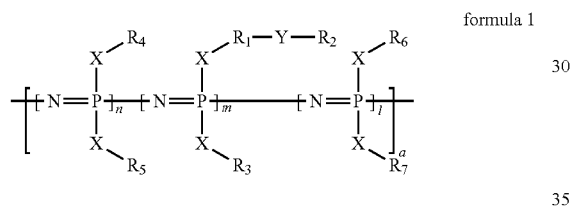

formula 1 wherein, a represents a degree of polymerisation of the poly(organo)phosphazenes in a range of 1 to 150;

m is an integer between 1 and 150;

n and l are the same or different and each of n and l is independently an integer between 0 and 149;

X represents O, S or NH;

Y represents a pH sensitive functional group, wherein the pH sensitive functional group is selected from the group consisting of hydrazide, hydroxamate, imine, cyclic acetal and aconityl;

$R_1$ is selected from the group consisting of ($C_1$ to $C_{10}$)-alkyl, ($C_1$ to $C_{10}$)-alkenyl, ($C_1$ to $C_{10}$)-alkynyl, ($C_1$ to $C_{10}$)-alkoxy, ($C_1$ to $C_{10}$)-alkenoxy, ($C_1$ to $C_{10}$)-acyl, cycloalkyl, cycloalkenyl, aryl, arylalkyl, arylalkenyl, ($C_1$ to $C_{10}$)-heteroalkyl, ($C_1$ to $C_{10}$)-heteroalkenyl, ($C_1$ to $C_{10}$)-heteroalkynyl, ($C_1$ to $C_{10}$)-heteroalkoxy, ($C_1$ to $C_{10}$)-heteroalkenoxy, ($C_1$ to $C_{10}$)-heteroacyl, heterocycloalkyl, heterocycloalkenyl, heteroaryl, heteroarylalkenyl, heteroarylalkyl, and polyalkylene oxide;

$R_2$ represents an anti-cancer drug;

$R_3$, $R_4$, $R_5$, $R_6$ and $R_7$ are the same or different and each of $R_3$, $R_4$, $R_5$, $R_6$ and $R_7$ is independently selected from the group consisting of $R_1$—Y—$R_2$, polyalkylene oxide, depsipeptide, amino acid alkyl ester, and a tumor targeting ligand.

2. The poly(organo)phosphazene molecule conjugate according to claim 1, wherein the pH sensitive group "Y" within formula 1 is represented by a moiety between $R_1$ and $R_2$ of one formula selected from the group consisting of formula 2 to 7:

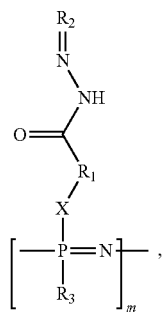

formula 2

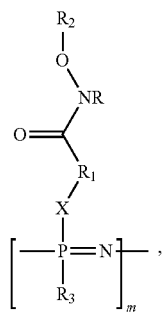

formula 3

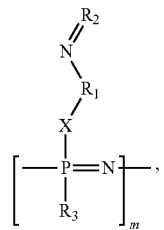

formula 4

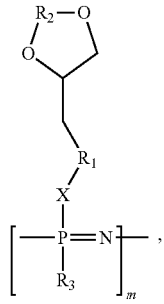

formula 5

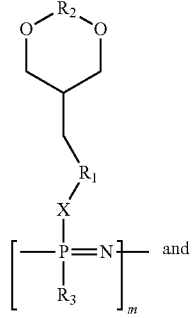

formula 6 and

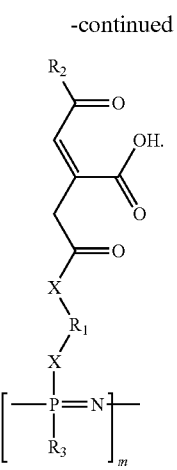

formula 7

3. The poly(organo)phosphazene molecule conjugate according to claim 1, wherein a sum of a, m, n, and l is ≤150.

4. The poly(organo)phosphazene molecule conjugate according to claim 1, wherein n and l are the same or different and each of n and l is independently an integer between 1 to 149.

5. The poly(organo)phosphazene molecule conjugate according to claim 1, wherein X is NH.

6. The poly(organo)phosphazene molecule conjugate according to claim 1, wherein the anti-cancer drug is selected from the group consisting of antibiotics, si-RNA, antisense RNA, alkylating agents, platinum analogues, intercalating drugs, mitotic inhibitors, taxanes, topoisomerase inhibitors, anti-metabolites, hydroxycarbamid, podophyllotoxin, enzymes, hormones, tumor necrosis factor, biological response modifiers and any other known cytotoxic drug.

7. The poly(organo)phosphazene molecule conjugate according to claim 1, wherein the polyalkylene oxide is selected from the group consisting of polyether, methoxypolyether, ethoxypolyether, polyethylene oxide, polypropylene oxide, polybutylene oxide, polyethylene glycol, polypropylene glycol, polybutylene glycol, methoxypolyethylene oxide, methoxypolypropylene oxide, methoxypolybutylene oxide, methoxypolyethylene glycol, methoxypolypropylene glycol, methoxypolybutylene glycol, ethoxypolyethylene oxide, ethoxypolypropylene oxide, ethoxypolybutylene oxide, ethoxypolyethylene glycol, ethoxypolypropylene glycol, ethoxypolybutylene glycol, poly(ethylene oxide-co-propylene oxide), poly(ethylene glycol-copropylene glycol), poly(ethylene oxide-co-butylene oxide), poly(ethylene glycol-co-butylene glycol), poly(propylene oxide-co-butylene oxide), poly(propylene glycol-co-butylene glycol), methoxypoly(ethylene oxide-co-propylene oxide), methoxypoly(ethylene glycol-co-propylene glycol), methoxypoly(ethylene oxide-co-butylene oxide), methoxypoly(ethylene glycol-cobutylene glycol), methoxypoly(propylene oxide-co-butylene oxide), methoxypoly(propylene glycol-co-butylene glycol), ethoxypoly(ethylene oxide-co-propylene oxide), ethoxypoly(ethylene glycol-co-propylene glycol), ethoxypoly(ethylene oxide-co-butylene oxide), ethoxypoly(ethylene glycol-co-butylene glycol), ethoxypoly(propylene oxide-co-butylene oxide) and ethoxypoly(propylene glycol-co-butylene glycol).

8. The poly(organo)phosphazene molecule conjugate according to claim 1, wherein the depsipeptide is a peptide in which one or more of the amide (—CONHR—) bonds are replaced by ester (COOR) bonds.

9. The poly(organo)phosphazene molecule conjugate according to claim 1, wherein the depsipeptide is selected from the group consisting of beativericin, morpholinedione, valinomycin, Depsipeptide A, Depsipeptide B, ethyl-2-(O-glycyl)glycolate and ethyl-2-(O-glycyl)lactate.

10. The poly(organo)phosphazene molecule conjugate according to claim 1, wherein the amino acid alkyl ester is an ester of an amino acid and a ($C_1$ to $C_{10}$)-alkanol.

11. The poly(organo)phosphazene molecule conjugate according to claim 1, wherein the tumor-targeting ligand is selected from the group consisting of biotin, folic acid, vitamin B12, riboflavin, hyaluronic acid, monoclonal antibodies targeting tumor-specific antigens and/or tumor-specific receptors and variants thereof, polyunsaturated fatty acids, aptamers targeting tumor-specific antigens and/or tumor-specific receptors, and oligopeptides targeting tumor-specific antigens and/or tumor-specific receptors.

12. The poly(organo)phosphazene molecule conjugate according to claim 1, wherein the poly(organo)phosphazene molecule conjugate has a polydispersity of 1.8 or less.

13. A process for preparing a poly(organo)phosphazene molecule conjugate according to claim 1, comprising the steps of:
   a) preparing dichloropolyphosphazene by initiating living cationic polymerization of chlorophosphoranimines;
   b) substituting at least one chlorine atom of the dichloropolyphosphazene of step a) with a pH sensitive linker; and
   c) performing a reaction for covalently binding an anti-cancer drug to the pH sensitive linker.

14. The process according to claim 13, wherein the polymerised dichloropolyphosphazene of step a) has a polydispersity of 1.8 or less.

15. The process according to claim 13, further comprising the step of substitution of at least one chlorine atom with a polyalkylene oxide between steps b) and c).

16. The process according to claim 13, further comprising the step of substitution of at least one chlorine atom with a depsipeptide between steps b) and c).

17. The process according to claim 13, further comprising the step of substitution of at least one chlorine atom with an amino acid alkyl ester between steps b) and c).

18. The process according to claim 13, further comprising the step of substitution of at least one chlorine atom with a tumor targeting ligand between steps b) and c).

19. A poly(organo)phosphazene molecule conjugate obtained by a process of:
   a) preparing dichloropolyphosphazene by initiating living cationic polymerization of chlorophosphoranimines;
   b) substituting at least one chlorine atom of the dichloropolyphosphazene of step a) with a pH sensitive linker; and
   c) performing a reaction for covalently binding an anti-cancer drug to the pH sensitive linker.

20. A pharmaceutical composition comprising a polyorganophosphazene according to claim 1 and a pharmaceutically acceptable carrier.

21. A method of treatment of cancer comprising administering a poly(organo)phosphazene molecule conjugate according to claim 1 to a patient in need thereof.

22. The method according to claim 21, wherein the poly(organo)phosphazene molecule conjugate is administered intravenously.

* * * * *